(12) United States Patent
Hui et al.

(10) Patent No.: US 7,323,302 B2
(45) Date of Patent: Jan. 29, 2008

(54) MOLECULAR MARKERS

(75) Inventors: Kam Man Hui, Singapore (SG); Qing Cheng, Memphis, TN (US)

(73) Assignee: Singapore Health Services Pte, Ltd, Singapore (SG)

( * ) Notice: Subject to any disclaimer, the term of this patent is extended or adjusted under 35 U.S.C. 154(b) by 444 days.

(21) Appl. No.: 10/333,895

(22) PCT Filed: Jul. 26, 2001

(86) PCT No.: PCT/AU01/00910

§ 371 (c)(1),
(2), (4) Date: Aug. 29, 2003

(87) PCT Pub. No.: WO02/08419

PCT Pub. Date: Jan. 31, 2002

(65) Prior Publication Data

US 2004/0053261 A1 Mar. 18, 2004

(30) Foreign Application Priority Data

Jul. 26, 2000 (AU) .................................... PQ9017

(51) Int. Cl.
*C12Q 1/68* (2006.01)
(52) U.S. Cl. ........................................................ 435/6
(58) Field of Classification Search ...................... 435/6
See application file for complete search history.

(56) References Cited

OTHER PUBLICATIONS

Tockman et al (Cancer Res., 1992, 52:2711s-2718s).*
Sales et al (The Journal of Clinical Endocrinology and Metabolism, May 2001, 86(5): 2243-2249).*
Muller et al (JNCI, Mar. 18, 1998, 90(6):433-439).*
Shim, C., et al., "Profiling of Differentially Expressed Genes in Human Primary Cervical Cancer . . . ," Clinical Cancer Research, 4:3045-3050, (1998).
Nees, M., et al., "Identification of novel molecular markers which correlate with HPV-induced tumor progression," Oncogene, 16:2447-2458, (1998).
Huang, G.M., et al., "Prostate Cancer Expression Profiling by cDNA Sequencing Analysis," Genomics, 59:178-186, (1999).
Cheng, Q., et al., "Identification and Characterization of Genes Involved in the Carcinogenesis of Human . . . ," Int. J. Cancer, 98:419-426, (2002).
EMBL Accession No. XP-002363719 "*Homo sapiens* cDNA clone," NCI-CGAP, Jun. 24, 1997.
Embl Accession No. XP-002363720, "*Homo sapiens* genomic clone RPCI-11-274E21, genomic survey sequence," Zhao, S., et al., Apr. 29, 1999.

Bae, M-K, "Identification of Genes Differentially Expressed by Hypoxia in Hepatocellular Carcinoma Cells," Biochem. Biophys. Res. Comm. 243:158-162, (1998).
Hashimoto, Y., et al., "Identification of Genes Differentially Expressed in Association with Metastatic Potential of K-1735 . . . ," Cancer Res., 56:5266-5271, (1996).
Fung, L.F., et al., "Identification of genes differentially expressed in nasopharyngeal carcinoma by messenger . . . ," International Journal of Oncology, 13:85-89, (1998).
EMBL Accession No. AL117339, "Human DNA sequence from clone RP11-508N22 on chromosome 10 . . . ," Wilson, S., Sep. 10, 1999.
EMBL Accession No. AL035705, "Human DNA sequence from clone RP4-758N20 on chromosome 1p31.3-32.2 . . . ," Cobley, V., Mar. 12, 1999.
Hattori, M., et al., "The DNA sequence of human chromosome 21," Nature, 405:311-319, (2000).
Hart, M.C., et al., "Vertebrates Have Conserved Capping Protein alpha Isoforms With Specific Expression Patterns," Cell Motility and the Cytoskeleton, 38:120-132, (1997).
Yang, X., et al., "Identification of two novel cellular genes associated with multistage carcinogenesis of human . . . ," Carcinogenesis, 17:563-567, (1996).
Lee, J-W., et al., "Differential Display and Cloning of Messenger RNA from Human Normal Nasal Epithelial Cells Versus . . . ," Chinese J. Microbiol. Immunol. 29:225-231, (1996).

* cited by examiner

*Primary Examiner*—Misook Yu
*Assistant Examiner*—Sean E Aeder
(74) *Attorney, Agent, or Firm*—Dann, Dorfman, Herrell & Skillman, P.C.; Kathleen D. Rigaut

(57) ABSTRACT

The present invention relates generally to genetic sequences exhibiting differential expression patterns in cancer tissue relative to normal tissue. The identification of differentially expressed genetic sequences permits their use as molecular markers for cancer, as early indicators of cancer progression and/or as predictive markers for a propensity or likelihood of a cancer to develop. The present invention relates particularly to genetic sequences exhibiting expression patterns up-regulated in cervical cells or associated with pre-, early- or late-onset cervical cancer relative to normal cervical cells. The genetic sequences of the present invention provide markers for early- or late-onset cervical cancer and/or a cancer related to cervical cancer. The markers of the present invention further provide potential targets for the development of therapeutic protocols for the treatment or prophylaxis of cervical or related cancer. Such therapeutic protocols are directed to inhibiting expression of the marker or inhibiting the expression product of the marker. The present invention is further directed to a method for identifying molecular markers which are useful indicators of cervical cancer and/or its progression.

9 Claims, 11 Drawing Sheets

```
(1B)
(1B)
(1B)
(2A)
(2A)
(2B)
(2B)
(3B)
(3B)
```

| | | | | | | | | | | Clone | Best match in GenBank Database |
|---|---|---|---|---|---|---|---|---|---|---|---|
| 7 | 8 | 9 | 10 | 11 | 12 | 13 | 14 | 15 | 16 | | |

```
G30CA   - human 16S ribosomal RNA
G30CB   - human EST vu04f09
G30CC   - human ribosomal protein S12 (RPS12) mRNA
G30CD   - human mRNA for collagenase
G30CE   - no match
G30CH   - human ZNF01 and HUMORFKG1B genes
G30CI   - human guanine nucleotide binding protein beta 5 (GNB5)
G30CJ   - human ribosomal protein L13a (RPL13A) mRNA
G30CK   - no match
G30CM   - human chromosome X clone RP1-298J18
G31N1   - no match
G31C1   - human STS WI-15569
G31C2   - no match
G31C3   - no match
G31C4A  - human GAP-associated tyrosine phosphoprotein p62 mRNA
G31C4B  - homo sapiens chromosome 1 clone RP4-758N20
G31C4C  - no match
G31C5A  - human transmembrane protein BRI (BRI) mRNA
G31C5B  - no match
G31C5C  - no match
G31C5E  - human capping protein (actin filament) muscle Z-line alpha-1 mRNA
G31C5G  - no match
G31C5H  - human gene for casein kinase II subunit beta
G31C6A  - human L-3-phosphoserine-phosphatase homo (C09) mRNA
G31C6B  - human EST zh46b08.s1
G32N    - no match
G32C2B  - human general transcription factor IIB (GTF2B) mRNA
G32C2C  - human clone 3A ETS-like protein mRNA
G32C3A  - human cDNA FLJ10841 fis, clone NT2RP4001339
G32C3B  - human NADH dehydrogenase subunit 6
G32C3C  - no match
G32C4A  - human mRNA for KIAA1311 protein
G32C4B  - human NADH dehydrogenase subunit 4
G32C4C  - no match
G32C4D  - no match
G32C4E  - human chromosome 17 clone HCIT48C15
G32C5A  - no match
G32C5B  - human SDH003 mRNA
G32C6   - human ubiquitin specific protease 3 (USP3) mRNA
G32C7   - human proline 4-hydroxylase, alpha 1 (P4HA1) mRNA
beta-2-microglobulin
alpha-tubulin
cyclophilin
beta-actin
beta-actin
ubiquitin
ubiquitin
G3PDH
G3PDH
G3PDH
```

Figure 2

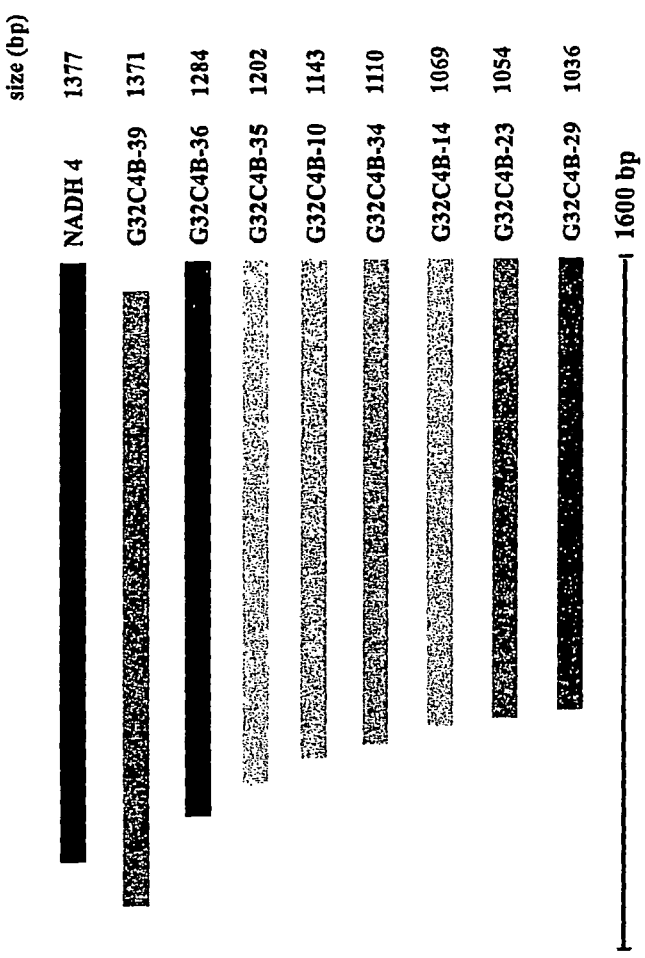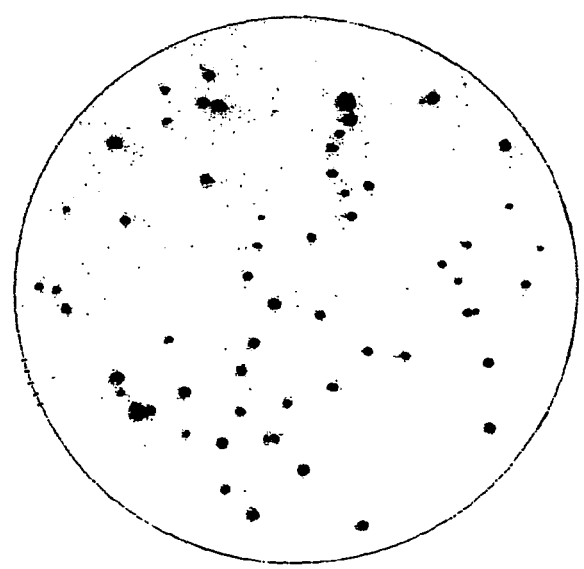
All positive clones selected by G32C4B probe were homology to NADH 4
The positive clones obtained from HeLa cell cDNA library with G32C4B probe using ClonCapture cDNA Selection Kit
Figure 4

Summary:

| cancer stage | patient number | tissue | G32C4B net probe volume | G32C4B net fold increase | G30CC net probe volume | G30CC net fold increase |
|---|---|---|---|---|---|---|
| 1B | 61 | normal | 640 | | 844 | |
| | | cancer | 2801 | 4.39 | 2442 | 2.90 |
| | 85 | normal | 887 | | 1118 | |
| | | cancer | 4996 | 5.63 | 5106 | 4.57 |
| | 86 | normal | 913 | | 690 | |
| | | cancer | 5541 | 6.07 | 1310 | 1.90 |
| | 87 | normal | 717 | | 787 | |
| | | cancer | 3462 | 4.83 | 1883 | 2.39 |
| 2A | 55 | normal | 523 | | 1438 | |
| | | cancer | 1076 | 2.06 | 10120 | 7.04 |
| | 40 | normal | 573 | | 333 | |
| | | cancer | 961 | 1.68 | 1198 | 3.60 |
| | 69 | normal | 298 | | 279 | |
| | | cancer | 698 | 2.35 | 1526 | 5.48 |
| 2B | 42 | normal | 984 | | 2200 | |
| | | cancer | 920 | 0.93 | 2168 | 0.99 |
| | 71 | normal | 1208 | | 3043 | |
| | | cancer | 980 | 0.81 | 3567 | 1.17 |
| 3B | 77 | normal | 2491 | | 979 | |
| | | cancer | 721 | 0.29 | 571 | 0.58 |
| | 91 | normal | 6281 | | 7717 | |
| | | cancer | 5563 | 0.89 | 1845 | 0.24 |

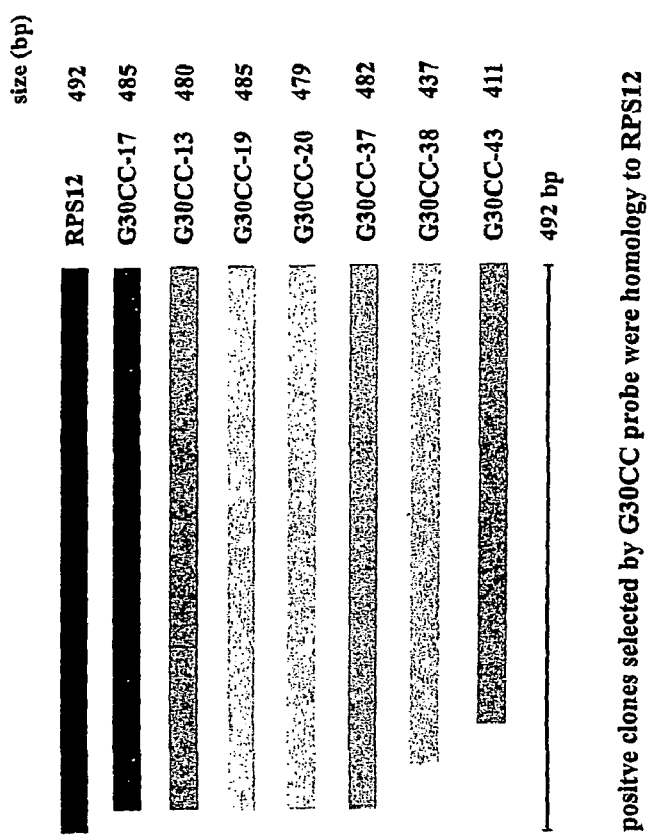
All positive clones selected by G30CC probe were homology to RPS12
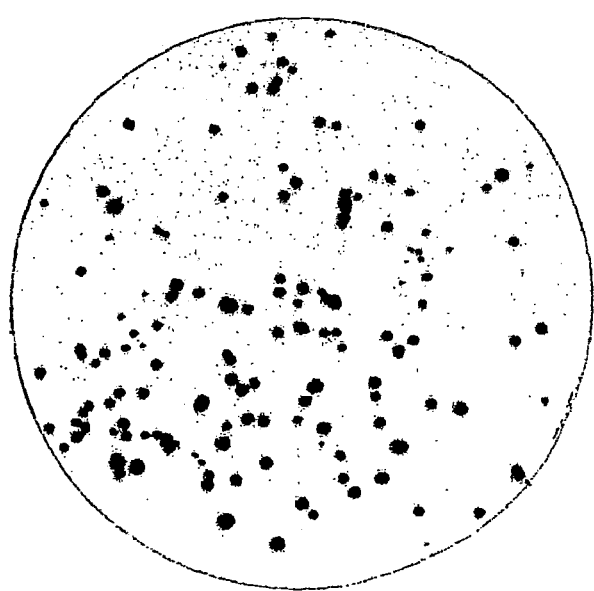
The positive clones obtained from HeLa cell cDNA library with G30CC probe using ClonCapture cDNA Selection Kit
Figure 6

Summary:

| cancer stage | patient number | tissue | G32C7 | | G30CA | |
|---|---|---|---|---|---|---|
| | | | net probe volume | net fold increase | net probe volume | net fold increase |
| 1B | 61 | normal | 102 | | 1974 | |
| | | cancer | 442 | 4.32 | 4695 | 2.38 |
| | 79 | normal | 197 | | 1651 | |
| | | cancer | 493 | 2.50 | 4346 | 2.63 |
| 2A | 90 | normal | 88 | | 1307 | |
| | | cancer | 362 | 4.11 | 5712 | 4.38 |
| 2B | 70 | normal | 657 | | 1133 | |
| | | cancer | 2009 | 3.06 | 1136 | 1.00 |
| | 71 | normal | 319 | | 1694 | |
| | | cancer | 1604 | 5.03 | 1459 | 0.86 |
| 3B | 91 | normal | 897 | | 1980 | |
| | | cancer | 510 | 0.57 | 3398 | 1.72 |
| | 73 | normal | 334 | | 10866 | |
| | | cancer | 291 | 0.87 | 1798 | 0.17 |

Summary:

| cancer stage | patient number | tissue | G31C5G | |
|---|---|---|---|---|
| | | | net probe volume | net fold increase |
| 1B | 79 | normal | 1184 | |
| | | cancer | 4235 | 3.59 |
| 2A | 81 | normal | 2756 | |
| | | cancer | 10018 | 3.64 |
| 2B | 71 | normal | 1081 | |
| | | cancer | 1003 | 0.93 |
| 3B | 77 | normal | 2665 | |
| | | cancer | 949 | 0.35 |

| cancer stage | patient number | tissue | G30CI | | G32C2B | |
|---|---|---|---|---|---|---|
| | | | net probe volume | net fold increase | net probe volume | net fold increase |
| 1B | 79 | normal | 197 | | 1887 | |
| | | cancer | 328 | 1.67 | 2798 | 1.48 |
| 2A | 81 | normal | 294 | | 682 | |
| | | cancer | 101 | 0.34 | 1026 | 1.51 |
| 2B | 71 | normal | 209 | | 1144 | |
| | | cancer | 98 | 0.47 | 1064 | 0.93 |
| 3B | 77 | normal | 462 | | 2070 | |
| | | cancer | 124 | 0.27 | 1301 | 0.63 |

SEQUENCE LISTING

<160> NUMBER OF SEQ ID NOS: 31

<210> SEQ ID NO 1
<211> LENGTH: 16

```
<212> TYPE: DNA
<213> ORGANISM: Artificial Sequence
<220> FEATURE:
<223> OTHER INFORMATION: Primer

<400> SEQUENCE: 1
gttttttttt ttcgaa                                                        16

<210> SEQ ID NO 2
<211> LENGTH: 13
<212> TYPE: DNA
<213> ORGANISM: Artificial Sequence
<220> FEATURE:
<223> OTHER INFORMATION: Primer

<400> SEQUENCE: 2
aagcttggtg aca                                                           13

<210> SEQ ID NO 3
<211> LENGTH: 13
<212> TYPE: DNA
<213> ORGANISM: Artificial Sequence
<220> FEATURE:
<223> OTHER INFORMATION: Primer

<400> SEQUENCE: 3
aagcttagtc aag                                                           13

<210> SEQ ID NO 4
<211> LENGTH: 13
<212> TYPE: DNA
<213> ORGANISM: Artificial Sequence
<220> FEATURE:
<223> OTHER INFORMATION: Primer

<400> SEQUENCE: 4
aagcttccac agc                                                           13

<210> SEQ ID NO 5
<211> LENGTH: 204
<212> TYPE: DNA
<213> ORGANISM: Artificial Sequence
<220> FEATURE:
<223> OTHER INFORMATION: Synthetic Sequence

<400> SEQUENCE: 5
aagcttggtg acagctggtt gtccaagata gaatcttagt tcaactttaa atttgcccac        60
agaaccctct aaatcccctt gtaaatttaa ctgttagtcc aaagaggaac agctctttgg       120
acactaggaa aaaaccttgt agagagagta aaaaatttaa cacccatagt aggcctaaaa       180
gcagccacca aaaaaaaaaa gctt                                              204

<210> SEQ ID NO 6
<211> LENGTH: 207
<212> TYPE: DNA
<213> ORGANISM: Artificial Sequence
<220> FEATURE:
<223> OTHER INFORMATION: Synthetic Sequence

<400> SEQUENCE: 6
aagcttggtg acatagtatg gtaataacaa tcatcaaaca tctttagttg acaagaattt        60
gaaatggata gtggggccgg gcgcagtggc tcatgctgta atcccagcaa taagtgaggc       120
ctagatgagc aaatcactgg agcccagaag ttcgagacca gcctgagcaa catgacgaaa       180
```

```
ccccgtctct acaaaaaaaa aaagctt                                       207
```

<210> SEQ ID NO 7
<211> LENGTH: 204
<212> TYPE: DNA
<213> ORGANISM: Artificial Sequence
<220> FEATURE:
<223> OTHER INFORMATION: Synthetic Sequence

<400> SEQUENCE: 7

```
aagcttggtg acaacaagaa actaggagaa tgggtaggcc tttgtaaaat tgacagagag    60
gggaaacccc gtaaagtggt tggttgcagt tgtgtagtag ttaaggacta tggcaaggag   120
tctcaggcca aggatgtcat tgaagagtat ttcaaatgca agaaatgaag aaataaatct   180
ttggctcaca aaaaaaaaaa gctt                                         204
```

<210> SEQ ID NO 8
<211> LENGTH: 207
<212> TYPE: DNA
<213> ORGANISM: Artificial Sequence
<220> FEATURE:
<223> OTHER INFORMATION: Synthetic Sequence

<400> SEQUENCE: 8

```
aagcttggtg acaaacatat cctttcaaga cagaaagaga caggagacat gagtctttgc    60
cggagaaaag cagctcaaga acacatgtgc agtcactggt gtcaccctgg ataggcaagg   120
gataactctt ctaacacaaa ataagtgttt tatgtttgga ataaagtcaa ccttgtttct   180
actgttttat acaaaaaaaa aaagctt                                      207
```

<210> SEQ ID NO 9
<211> LENGTH: 206
<212> TYPE: DNA
<213> ORGANISM: Artificial Sequence
<220> FEATURE:
<223> OTHER INFORMATION: Synthetic Sequence

<400> SEQUENCE: 9

```
aagcttggtg acaggaatag aaaatggtac agccactgtg ggaaacagtt tggcagttct    60
ttagaaagct gaacatagaa ttaccatagg atctagcagt tcttctaggt acataccccca  120
aagaattgaa agcaaggact tgaacagata tttgtacacc catgttcata gcagcagttt   180
tcacaacagc caaaaaaaaa aagctt                                       206
```

<210> SEQ ID NO 10
<211> LENGTH: 202
<212> TYPE: DNA
<213> ORGANISM: Artificial Sequence
<220> FEATURE:
<223> OTHER INFORMATION: Synthetic Sequence

<400> SEQUENCE: 10

```
aagcttggtg acactgagca aataaatatg ttgagaatga tgacagcaag atttctccat    60
tagagaaggt atttataaaa ataggaatga ggagagctag aaaccctgga gtgtggcatt   120
agaatagaac tcatatcttt taaatatata ggaacaaata aataaattgt tgtgtgtgca   180
catatgcaaa aaaaaaagc tt                                            202
```

<210> SEQ ID NO 11
<211> LENGTH: 207
<212> TYPE: DNA
<213> ORGANISM: Artificial Sequence -continued

```
<220> FEATURE:
<223> OTHER INFORMATION: Synthetic Sequence

<400> SEQUENCE: 11
aagcttggtg acaagaaagc catggtgtgg gacatgcgct ccggccagtg cgtgcaggcc    60
tttgaaacac atgaatccga catcaacagt gtccggtact accccagtgg agatgccttt   120
gcttcagggt cagatgacgc tacgtgtcgc ctctatgacc tgcgggcaga tagggaggtt   180
gccatctatt ccaaaaaaaa aaagctt                                      207

<210> SEQ ID NO 12
<211> LENGTH: 206
<212> TYPE: DNA
<213> ORGANISM: Artificial Sequence
<220> FEATURE:
<223> OTHER INFORMATION: Synthetic Sequence

<400> SEQUENCE: 12
aagcttggtg acatagcaag actctgtcta aaaaaaaaaa aaaaaacct actataggcc    60 tgcaatagtg cctcatgcct gtaatcccag cactatggga ggccaaagtg ggaggattgc   120
ttgagactag gagtttgaga ccagcctggg aacataacg tgaccctgtt tctaccaaca   180 cccccgccc caaaaaaaaa aagctt                                       206

<210> SEQ ID NO 13
<211> LENGTH: 258
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, t, or g

<400> SEQUENCE: 13
aagcttagtc aagnggaagg aattgataca aaannnngag gggctaatta tagaanncaa    60
gtcccttcgt aggtgtggga gataatccag tgcataattg gaggagttag tctttnaaag   120
tatatgacca tggagtggtt ggctgtgtgt ggtggaagaa aagataatta gaaatgcagg   180
cattcaaaga acttaaaggc catatgttaa gatattttaa gccttaagac tggatgngtt   240
accaaaaaaa aaaagctt                                                258

<210> SEQ ID NO 14
<211> LENGTH: 254
<212> TYPE: DNA
<213> ORGANISM: Artificial Sequence
<220> FEATURE:
<223> OTHER INFORMATION: Synthetic Sequence

<400> SEQUENCE: 14
aagcttagtc aagtacatta aatggcattc aagttgaaaa agaagttaaa ctatctgttt    60
acaaatgaca tgatcttatc tatagaaaat cacaagggaa atcacaaaaa tctgttaaaa   120
ctaatgatcg agttcagcaa gttgcagaat acaagttcaa tatacataaa tatatttcta   180
gacagttgca atgaacatac aaaaatgaaa ttacaaaaaa cggttgttac caataactca   240
aaaaaaaaaa gctt                                                    254

<210> SEQ ID NO 15
<211> LENGTH: 183
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t

<400> SEQUENCE: 15
aagcttagtc aagaggcata aaggtttagc angttaaggc agagatatag atgntttttta    60 gaaaggtcta aatacaattc ctagaaanaa aaatatactg agattatcag attatgcatt   120
gcagaaggtt agattagtga tcttgaagac ataatcatag aatgtatcaa aaaaaaaaag   180
ctt                                                                 183

<210> SEQ ID NO 16
<211> LENGTH: 176
<212> TYPE: DNA
<213> ORGANISM: Artificial Sequence
<220> FEATURE:
<223> OTHER INFORMATION: Synthetic Sequence

<400> SEQUENCE: 16
aagcttagtc aaggcaaaat aacaaaagga ttaaaaataa aataatggcc agcaatatat    60
cagaaaacaa acagggaaa gaaatcagtt agctgaccta gatctcagac aaagtagaaa   120
ataagacaaa acactttctc ccctcatctc tgctcacccc caaaaaaaaa aagctt       176

<210> SEQ ID NO 17
<211> LENGTH: 179
<212> TYPE: DNA
<213> ORGANISM: Artificial Sequence
<220> FEATURE:
<223> OTHER INFORMATION: Synthetic Sequence

<400> SEQUENCE: 17
aagcttagtc aagcaagttt gttccaggtg acccattgag ctgtgtatgc attttttgttt   60 atttcaataa aatatatttg tattatttgt ccttcatact atccatccat accacactat   120
cttctgtatc aggtagtcta atagaaatat acctgttttg ttccaaaaaa aaaaagctt   179

<210> SEQ ID NO 18
<211> LENGTH: 179
<212> TYPE: DNA
<213> ORGANISM: Artificial Sequence
<220> FEATURE:
<223> OTHER INFORMATION: Synthetic Sequence

<400> SEQUENCE: 18
aagcttagtc aagaggaaga ggtaatgcct ttaagttaaa ggccggtcaa acacgatgac    60
tcacacctgt aattccacta taaataacta aggcaggagg atcacttgag cctaggagtt   120
tgagacagcc taaataacac agcaagacgg tgtctccata tatcaaaaaa aaaaagctt   179

<210> SEQ ID NO 19
<211> LENGTH: 242
<212> TYPE: DNA
<213> ORGANISM: Artificial Sequence
<220> FEATURE:
<223> OTHER INFORMATION: Synthetic Sequence

<400> SEQUENCE: 19
aagcttagtc aaggataacg cctaaatggt atatcactga ttttgtagag ctgctgggag    60
aaccggaaga ataacatcca ttgtcataca gctccaaaca acttcagatg aatttttaca   120
```

-continued

```
agttacacag attgatactg tttgcttaca attgcctatt acaacttgct atagaaagtt      180
ggtacagatg atctgcactg tcaagtaaac tacagttagg aatcctcaaa aaaaaaaagc      240
tt                                                                     242

<210> SEQ ID NO 20
<211> LENGTH: 243
<212> TYPE: DNA
<213> ORGANISM: Artificial Sequence
<220> FEATURE:
<223> OTHER INFORMATION: Synthetic Sequence

<400> SEQUENCE: 20
aagcttagtc aaggtatcaa gattttcttc atgccattac tacagaaaca gggtagaata      60
ctcatagttc ttcggctcaa gagcagcaga gagtttctga caagtatttt tgcatttggt     120
aaaatggtag tctaagttgg aactcagtaa actattttg ttttcaatga ggggaagtgt      180
agaactgtag tactctcaaa ttatttttc tcaaattggc ctttgtgcaa aaaaaaaag       240 ctt                                                                    243

<210> SEQ ID NO 21
<211> LENGTH: 312
<212> TYPE: DNA
<213> ORGANISM: Artificial Sequence
<220> FEATURE:
<223> OTHER INFORMATION: Synthetic Sequence

<400> SEQUENCE: 21
aagcttccac agcacctgtg tatacttcca ttatggcatg taacatgctg gcaagaaatt      60
gattcattgg gttgtgtctt ctcagctgcc tgaagaatga atcatatac tctagtttca     120 tatgcccagc attgtacaca acttgacaca tcacagcagc tctaggaaag cacataggct     180
gacaactgag tgaacaaccc actgactgtg tgtcgttcag ggttgggaaa gcaagggcag     240
gtctctgtgc cccatctcta gcttttcctc aacttaggct ttataaaccc ttgcatcaaa     300
aaaaaaaagc tt                                                         312

<210> SEQ ID NO 22
<211> LENGTH: 311
<212> TYPE: DNA
<213> ORGANISM: Artificial Sequence
<220> FEATURE:
<223> OTHER INFORMATION: Synthetic Sequence

<400> SEQUENCE: 22
aagcttccac agctataaat tgaggcagct aacgtcaaat tcttgaatac aaaactttgc      60
ctgttgtaca tagcctatac aaaatgctgg gttgagcctt tcatgaggaa aaacaaaaga     120
catggtacgc attccagggc tgaatactat tgcttggcat tctgtatgta tatactatgt     180
gaaacatatt taatgattta aatttcttat caaatttctt ttgtagcaat ctaggaaacc     240
ggtattttgg aagatatttg aaattatgta attcttgaat aaacattttc gaactcaaaa     300
aaaaaaagct t                                                          311

<210> SEQ ID NO 23
<211> LENGTH: 284
<212> TYPE: DNA
<213> ORGANISM: Artificial Sequence
<220> FEATURE:
<223> OTHER INFORMATION: Synthetic Sequence
<220> FEATURE:
```

```
<221> NAME/KEY: misc_feature
<222> LOCATION: (0)...(0)
<223> OTHER INFORMATION: n = a, c, t, or g

<400> SEQUENCE: 23
aggcagccgg actccctgtc tcacctacat taacccatgc atactgtatg ccaataaact      60
cactttggta tatccggcgt cacatgcaga gaggaactct gcgngncaaa gtgttgcttc     120
ttaaagtttc attattggca actagagggt tgttttaat gcatgaaac taaacagatt      180 cctcggggag ttcctgaagg aaccaggtgg gcaaacctt gcttatatac atgcggcctc     240
acctggaaga gaaataaacc acttgtacca aaaaaaaaaa gctt                     284

<210> SEQ ID NO 24
<211> LENGTH: 307
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (0)...(0)
<223> OTHER INFORMATION: n = a, c, g, or t

<400> SEQUENCE: 24
aagcttccac agcatccatt gttgaaataa ccattttcag ttgtgatgcc ttaactaaga      60
agccaattgt tagcctgaaa tgcaatcttg gtagccagtt tcaatgaagc tagagattag    120
tcagaaaaag ttagctgttg ggctttagaa aggnnttttg agtcctgtca tttctacttg    180
ggagcatttt ggagcagatt agtctttcag tataaaaaca agtggctacc tgatggaaac    240
ttttcctacc cttataggaa actgagcaca agctgaatga tattgctgct gcaaaaaaaa    300
aaagctt                                                               307

<210> SEQ ID NO 25
<211> LENGTH: 310
<212> TYPE: DNA
<213> ORGANISM: Artificial Sequence
<220> FEATURE:
<223> OTHER INFORMATION: Synthetic Sequence

<400> SEQUENCE: 25
aagcttccac agcaccatcc tacctccatg ctaaccccac taaaacactc accagacctc      60 aaccctgac ccccatgcct caggatactc ctcaatagcc atcgctgtag tatacccaaa    120
gacaaccatc attcccccta aataaattaa aaaaactatt aaaccatat aacctccccc    180 aaaattcaga ataataacac acccgaccac accgctaaca accaatacta aaccccata     240 aataggagaa ggcttagaag aaaacccac aaaccccatt actaaaccca cactcaaaaa    300
aaaaaagctt                                                           310

<210> SEQ ID NO 26
<211> LENGTH: 303
<212> TYPE: DNA
<213> ORGANISM: Artificial Sequence
<220> FEATURE:
<223> OTHER INFORMATION: Synthetic Sequence

<400> SEQUENCE: 26
aagcttccac agcccactga ctcaaatggt aatctctttt ggcaacaccc acacagacac      60
acccaggatt aatactttgt atccctcatt ccaattaagt tgacactcag tattaaccat    120
catatatggc aacatatctt tctggatagg acctagagaa actttcaaat aatgacttgt    180
```

```
aacttctcta cactgaagga atatatacac aatttgtaat ttaattttga gtgtatattg    240
acaaactaca tgtatctaca aattacccttt aattcaattg caaccctcaa aaaaaaaag    300 ctt                                                                 303
```

<210> SEQ ID NO 27
<211> LENGTH: 260
<212> TYPE: DNA
<213> ORGANISM: Artificial Sequence
<220> FEATURE:
<223> OTHER INFORMATION: Synthetic Sequence

<400> SEQUENCE: 27

```
aagcttccac agccacagaa ctaatcatat tttatatctt cttcgaaacc acacttatcc     60
ccaccttggc tatcatcacc cgatgaggca accagccaga acgcctgaac gcaggcacat    120
acttcctatt ctacaccccta gtaggctccc ttcccctact catcgcacta atttacactc   180 acaacacccct aggctcacta acattctac tactcactct cactgcccaa gaactatcaa    240
actccaaaaa aaaaaagctt                                                260
```

<210> SEQ ID NO 28
<211> LENGTH: 264
<212> TYPE: DNA
<213> ORGANISM: Artificial Sequence
<220> FEATURE:
<223> OTHER INFORMATION: Synthetic Sequence

<400> SEQUENCE: 28

```
aagcttccac agcaccaaca aaagttaacg ttgcatgttt cactatttgg ttttaacct     60 acattccaaa tggcttttac aacagttata ataaatgat aactgcaaag gcattgtgta    120
gctaaatgaa atgttgtaa atgtgataat gaaacacggc caaagttttg acaattaggc    180
aatagatgga gataaaaatt ttagactaaa gtgtacaata aaatacacac acacagccaa   240
actcactcca aaaaaaaaa gctt                                            264
```

<210> SEQ ID NO 29
<211> LENGTH: 257
<212> TYPE: DNA
<213> ORGANISM: Artificial Sequence
<220> FEATURE:
<223> OTHER INFORMATION: Synthetic Sequence

<400> SEQUENCE: 29

```
aagcttccac agcaacaacc aacatagcta atacagaaag cagtcagcag actctacaga    60
attcccagtt tcttttaaca aggtagctca tttgttaata gaattttgtt tgggaagtaa   120
tattttattg ccactacagt ctggaattat cttttctctt ttgtgcatta tatttcttaa   180
aattttgtgt ttgattaaaa ctcacagatc tctgattaaa acgcatattc agtactttcc   240
ccaaaaaaaa aaagctt                                                   257
```

<210> SEQ ID NO 30
<211> LENGTH: 250
<212> TYPE: DNA
<213> ORGANISM: Artificial Sequence
<220> FEATURE:
<223> OTHER INFORMATION: Synthetic Sequence

<400> SEQUENCE: 30

```
aagcttccac agctataatg gacatcaggt tgactctaaa tcaaggatca tgtgtgcaca    60
```

-continued

```
atacttgtgg cccacaaaat ttcacaatga ctgctgagga atcattcttt ttgcctgtaa      120
aatataacaa agggcatcat taagtagacc aggtaattac tgcttgtctc tcaaggctgc      180
tgtctttatc agcactaact aaataaattt gttggttcag ttgtacttgt cctgcaaaaa      240
aaaaaagctt                                                            250

<210> SEQ ID NO 31
<211> LENGTH: 224
<212> TYPE: DNA
<213> ORGANISM: Artificial Sequence
<220> FEATURE:
<223> OTHER INFORMATION: Synthetic Sequence

<400> SEQUENCE: 31
aagcttccac agcagaggaa ttacaggtag caaattatgg agttggagga cagtatgaac       60
cccattttga ctttgcacgg aaagatgagc cagatgcttt caaagagctg gggacaggaa      120
atagaattgc tacatggctg ttttatatga gtgatgtgtc tgcaggagga gccactgttt      180
ttcctgaagt tggagctagt gtttggccca aaaaaaaaaa gctt                       224
```

MOLECULAR MARKERS

This application is a §371 filing of PCT/AU01/00910 filed 16 Jul. 2001, which in turn claims priority to Australian application PQ 9017, filed 26 Jul. 2000, the entire disclosures of each being incorporated by reference herein.

FIELD OF THE INVENTION

The present invention relates generally to genetic sequences exhibiting differential expression patterns in cancer tissue relative to normal tissue. The identification of differentially expressed genetic sequences permits their use as molecular markers for cancer, as early indicators of cancer progression and/or as predictive markers for a propensity or likelihood of a cancer to develop. The present invention relates particularly to genetic sequences exhibiting expression patterns up-regulated in cervical cells or associated with pre-, early- and/or late-onset cervical cancer relative to normal cervical cells. The genetic sequences of the present invention provide markers for pre-, early- or late-onset cervical cancer and/or a cancer related to cervical cancer. The markers of the present invention further provide potential targets for the development of therapeutic protocols for the treatment or prophylaxis of cervical or related cancer. Such therapeutic protocols are directed to inhibiting expression of the marker or inhibiting the expression product of the marker. The present invention is further directed to a method for identifying molecular markers which are useful indicators of cervical cancer and/or its progression.

BACKGROUND OF THE INVENTION

Bibliographic details of the publications referred to by author in this specification are collected at the end of the description.

The reference to any prior art in this specification is not, and should not be taken as, an acknowledgment or any form of suggestion that that prior art forms part of the common general knowledge in Australia.

Cervical carcinoma is one of the most common tumors affecting women world-wide, both in incidence and mortality, with approximately 471,000 new cases diagnosed and about 200,000 women die of the disease annually. (Pisani, et al., 1993 and 1997). In 1994, an estimated 15,000 women in the U.S. were diagnosed with invasive cervical carcinoma and approximately 4600 women died from this disease in the year despite remarkable progress made in screening (Boring et al., 1994). In 1995, the incidence increased to 15,800 cases and 4800 deaths in the U.S. (Wingo, et al., 1995).

Cervical carcinoma has its origins at the squamous-columnar junction either in the endocervical canal or on the portio of the cervix. The precursor lesion is dysplasia or carcinoma in situ (cervical intraepithelial neoplasia [CIN]), which can subsequently become invasive cancer. This process can be quite slow. It is proposed that 50% of dysplastic lesions disappear without treatment and 10% of dysplastic lesions reach the final stage of the intra-epithelial lesion prior to invasion of subjacent tissue. Only 2% of the total number of dysplasias progress beyond this intra-epithelial carcinoma to frank invasive cancer (Ostor, 1993; Duggan, 1998). However, longitudinal studies have shown that in untreated patients with in situ cervical cancer, 30-70% will develop invasive carcinoma over a period of 10-12 years. Only in about 10% of patients, lesions can progress from in situ to invasive in less than a year (Gustafsson, et al., 1989; Van Oortmarssen, et al., 1991).

With reference to cell types, cervical cancer can be classified into squamous cell carcinoma, adenocarcinoma, adenosquamous cell carcinoma and small cell carcinoma. Cellular Classification Squamous cell (epidermoid) carcinoma comprises approximately 80%, while adenosquamous and small cell carcinomas are relatively rare. However, among malignancies of the uterine cervix, the percentage of adenocarcinomas seems to have increased in recent reports, from 4.9-20% (Berek, et al., 1981; Goodman et al., 1989; Vizcaino, et al., 1998). Controversy remains over whether or not adenocarcinoma of the cervix carries a significantly worse prognosis than squamous cell carcinoma of the cervix (Steren et al., 1993). There are conflicting reports regarding the effect of adenosquamous cell type on outcome (Gallup et al., 1985; Yazigi et al., 1990). A report demonstrated that approximately 25% of apparent squamous tumors have demonstrable mucin production and behave more aggressively than their pure squamous counterparts suggesting that any adenomatous differentiation may confer a negative prognosis (Bethwaite et al., 1992). A study of patients with known invasive squamous carcinoma of the cervix found that over-expression of the c-myc oncogene was associated with poorer prognosis significance in early cervical carcinoma (Strang et al., 1987).

It is estimated that more than 6 million women in the U.S. have human papillomavirus (HPV) infection. Epidemiological studies convincingly demonstrate that the major risk factor for the development of pre-invasive or invasive carcinoma of the cervix is related to HPV infection. Studies (Brisson et al., 1994) suggest that acute infection with HPV types 16 and 18 conferred a one to 16.9-fold risk of rapid development of high-grade CIN. This far outweighs other known risk factors such as high parity, increasing number of sexual partners, young age at first intercourse, low socio-economic status and positive smoking history (Schiffman et al., 1993; Brisson et al., 1994). Although molecular techniques for the identification of HPV DNA are highly sensitive and specific, proper interpretation of these data is important. Some patients with HPV infection appear to be at minimal increased risk for development of cervical preinvasive and invasive malignancies while others appear to be at significant risk and candidates for intensive screening programs and/or early intervention. However, use of a positive HPV DNA test as the only parameter to dictate more in-depth evaluation of the patient may lead to unwarranted and ineffective treatment and/or unnecessary patient anxiety. Conversely, current technology may be too insensitive to detect small amounts of potentially tumorigenic HPV types leading to a false sense of security. Clearly the present recommendation for patients with an abnormal cervical cytology of a high-risk type (Bethesda Classification) should be thoroughly evaluated with colposcopy and biopsy. However, these tests are expensive and can be invasive.

Uterine cervical carcinogenesis has been recognized as a multi-stage process in which human papillornavirus (HPV) infection and other factors, such as somatic genetic alterations play a decisive role in the development of malignant cancer. The accumulation of cytogenetic abnormalities and chromosome structural aberrations or allele loss may lead to the selection of the final tumor phenotype, consistent with the long time that occurs between initial infection and tumor appearance (Herrington et al., 1995; Lazo, 1999).

Identification of these genes can be used for the cancer diagnosis and also to help stratify women into follow-up and treatment groups.

The prognosis for cervical cancer is markedly affected by the extent of disease at the time of diagnosis (Anton-Culver, et al., 1992). Among the major factors that influence prognosis are stage, volume and grade of tumor, histologic type, lymphatic spread, and vascular invasion (Werner-Wasik, et al., 1995). However, the molecular pathways leading to cervical dysplasia remain poorly understood. To gain a global view of the molecular events leading to tumour progression, the inventors have employed differential gene display as a systematic method to compare gene expression in human cervical cancer and matched normal tissues.

In work leading up to the present invention, the inventors identified differentially expressed DNA sequences which have corresponding RNA accumulated to higher levels in various stages of human cervical cancer. Activation of some of these genes in the early clinical stages of cervical cancer suggests their participation in pathways involved in the onset and/or progression of cancer providing diagnostic markers for the cervical cancer and targets for therapeutic intervention.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers SEQ ID NO:1, SEQ ID NO:2, etc. A sequence listing is provided after the claims.

The inventors utilize RT-PCR differential display analysis and cDNA microarrays to identify cellular genes involved in the multi-step carcinogenesis of squamous cell cervical carcinoma. cDNA clones are identified and cloned by differential gene expression display between cervical cancer biopsies and matched normal cervical tissues. These cDNA clones are consistently over-expressed in squamous cell cervical carcinoma biopsies of various FIGO stages using cDNA microarrays. Northern blot analysis and RNA-RNA in situ hybridization studies using cervical cancer biopsies of various FIGO stages is used to evaluate the role of these genes in disease progression. Two clones are identified as encoding NADH dehydrogenase 4 and ribosomal protein S12, respectively, when compared to sequences available in the GenBank database. The expression of these two genes is elevated in the matched normal tissues collected together with the late FIGO stages of cervical cancer biopsies. Increased expression of ribosomal protein S12 is also found in the immature basal epithelial cells of histo-pathological normal tissue collected from cervical cancer patients of early FIGO stages. In comparison, up-regulation of these two genes is not detected in cervical squamous epithelium collected from patients admitted for surgery for non-malignant conditions suggesting that expression of these two genes may have altered in the adjacent histo-pathologically "normal" cervical squamous epithelial tissue from cervical cancer patients. It is proposed that the ribosomal protein S12 and the NADH dehydrogenase 4 gene provide early diagnostic markers for human cervical cancer and to define a molecular margin for progressive disease Accordingly, an aspect of the present invention provides a method for detecting a molecular marker associated with normal or abnormal tissue from a mammal, said method comprising isolating total RNA from said abnormal tissue and corresponding tissue from a non-abnormal individual, generating complementary DNA molecules using reverse transcription-polymerase chain reaction (RT-PCR) and subjecting said DNA molecules to separation means such that the presence or absence or relative presence or absence of complementary DNA molecules can be detected from abnormal tissue relative to non-abnormal tissue wherein the presence or absence of a complementary DNA molecule in one type of tissue relative to another is indicative of a molecular marker associated with normal or abnormal tissue.

Another aspect of the present invention provides a method for identifying a molecular marker capable of distinguishing between a cancerous condition and a non-cancerous condition, said method comprising isolating total RNA from cancer tissue from an individual and from matched non-cancer tissue from another individual, generating complementary DNA molecules using RT-PCR and comparing said DNA molecules from said cancer and non-cancer tissue by gel electrophoresis wherein the presence or absence of a particular DNA species in cancer or non-cancer tissue relative to the other of non-cancer or cancer tissue, respectively is indicative of a molecular marker for said cancer.

Still another aspect of the present invention provides a genetic sequence comprising a sequence of nucleotides which is expressed differentially in cervical cancer cells relative to matched normal cervical epithelial cells.

A summary of sequence identifiers used throughout the subject specification is provided below.

SUMMARY OF SEQUENCE IDENTIFIERS

| SEQUENCE ID NO: | DESCRIPTION |
| --- | --- |
| 1 | Primer for identification of differentially displayed gene fragment P21 |
| 2 | Primer for identification of differentially displayed gene fragment P30 |
| 3 | Primer for identification of differentially displayed gene fragment P31 |
| 4 | Primer for identification of differentially displayed gene fragment 32 |
| 5 | Clone G30CA cDNA fragment |
| 6 | Clone G30CB cDNA fragment |
| 7 | Clone G30CC cDNA fragment |
| 8 | Clone G30CD cDNA fragment |
| 9 | Clone G30CE cDNA fragment |
| 10 | Clone G30CH cDNA fragment |
| 11 | Clone G30CI cDNA fragment |
| 12 | Clone G30CK cDNA fragment |
| 13 | Clone G31C4B cDNA fragment |
| 14 | Clone G31C4C cDNA fragment |
| 15 | Clone G31C5C cDNA fragment |
| 16 | Clone G31C5D cDNA fragment |
| 17 | Clone G31C5E cDNA fragment |
| 18 | Clone G31C5G cDNA fragment |
| 19 | Clone G31C6A cDNA fragment |
| 20 | Clone G31C6B cDNA fragment |
| 21 | Clone G32C2A cDNA fragment |
| 22 | Clone G32C2B cDNA fragment |
| 23 | Clone G32C2C cDNA fragment |
| 24 | Clone G32C3A cDNA fragment |
| 25 | Clone G32C3B cDNA fragment |
| 26 | Clone G32C3C cDNA fragment |
| 27 | Clone G32C4B cDNA fragment |
| 28 | Clone G32C4D cDNA fragment |
| 29 | Clone G32C5A cDNA fragment |
| 30 | Clone G32C6 cDNA fragment |
| 31 | Clone G32C7 cDNA fragment |

BRIEF DESCRIPTION OF THE FIGURES

FIG. 2 is a representation showing cDNA microarray analysis of the expression of 40 of the 44 cDNA clones isolated by differential display in different FIGO stags of human cervical squamous cell carcinoma biopsies. Data are presented in a matrix format: each row represents results obtained from a single cDNA clone and each column an experimental sample. Columns 1-10 represent the 10 cervical squamous cell carcinoma patients from which biopsies and matched normal epithelium were taken. The stages of disease are shown for each patient. For each sample, the ratio of the abundance of transcripts of each clone in the cancer biopsy to the abundance of the same clone's transcript detected in adjacent histo-pathologically normal epithelium tissues is represented by the color of the corresponding cell in the matrix. Green squares indicate transcript levels below the controls, red squares indicate transcript levels greater than that of the controls, while black squares indicate transcript levels equal to the controls. The controls used were β-2-microglobulin, α-tubulin, cyclophilin, β-actin, ubiquitin and G3PDH. Grey squares represent technically inadequate or missing data for that particular cell in the matrix.

FIG. 4 is a photographic representation showing cDNA library screening for the full-length cDNA of G32C4B. 53 positive clones were obtained using ClonCapture cDNA Selection Kit, from the Hela cDNA library with biotinylated G32C4B probe (A). 7 positive cDNA clones with longer insert captured by G32C4B probe were sequenced and were found to be homologous to the NADH dehydrogenase subunit 4 gene (more than 98% identical) throughout the lengths (B).

FIG. 6 is a photographic representation showing cDNA library screening for the full-length cDNA of G30CC. 122 positive clones were obtained using ClonCapture cDNA Selection Kit, from the Hela cDNA library with biotinylated G30CC probe (A). 7 positive cDNA clones with longer insert captured by G30CC probe were sequenced and were found to be homologous to the ribosomal protein S12 mRNA (more than 98% identical) throughout the lengths (B).

FIG. 12 is a photographic representation showing RNA-RNA in situ hybridization studies of clones G30CC and G32C4B with normal cervical squamous epithelium, cervical squamous cell carainoma adjacent epithelium collected from early to late FIGo and squamous cell carinoma biopsies. Consecutive tissue sections of 10 μm were hybridized to DIG-labeled anti-sense or sense probe derived from clone G30CC or G32C4B. Hematoxylin and Eosin staining was employed for employed for histology identification. Representative results obtained from clones G30CC and G32C4B to four different cervical tissue biopsies are presented. (A) Normal cervical squamous epithelium collected from non-malignant patient; (B) adjacent histo-pathological normal tissues obtained from an early stage cervical squamous cell carcinoma patient; (C) adjacent histo-pathological normal tissues obtained from a late stage cervical squamous cell carcinoma; and (D) a squamous cell biopsy section. The scale bar in the figures represent 80 μm. (BL, basal-layer epithelial cells; PL, par-layer epithelial cells; ST, stromal cells; SCC, squamous cell carcinoma.)

DETAILED DESCRIPTION OF THE PREFERRED EMBODIMENTS

Figure 1:
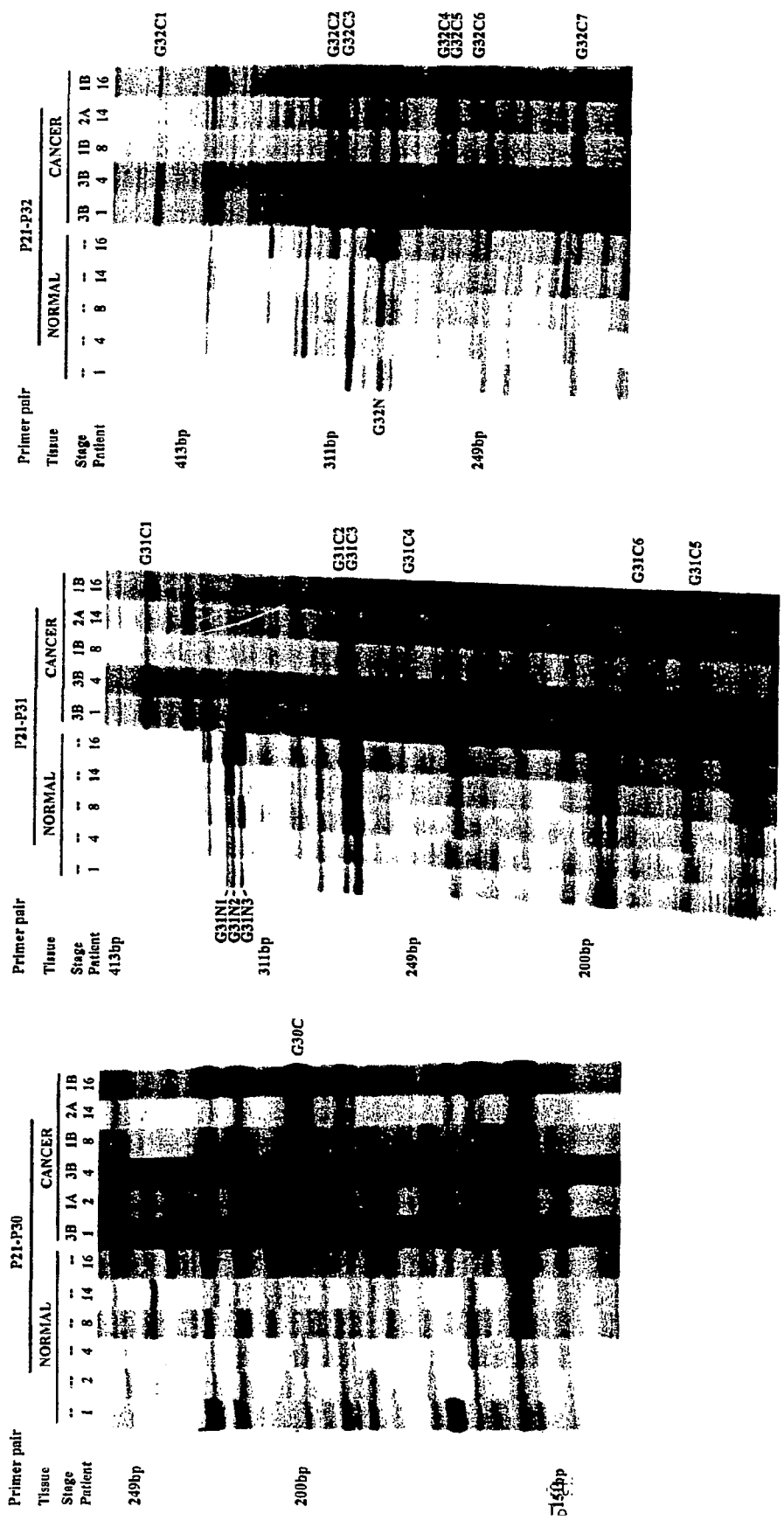
FIG. 1 is photographic representation showing differentially displayed analyzes of cDNA fragments of normal and human squamous cell carcinoma biopsies. One μg total RNA extracted from six cervical cancer biopsies and their matched normal tissue was reverse transcribed with P21 (3'-GTTTTTTTTTTTCGAA-5' [SEQ ID NO:1]) primer and subsequently amplified in parallel PCR in the presence of [$\alpha$-$^{33}$P]dATP by using P21 primer with either P30 (5'-AAGCTTGGTGACA-3' [SEQ ID NO:2]); P31 (5'-AAGCTTAGTCAAG-3' [SEQ ID NO:3]); or P32 (5'-AAGCTTCCACAGC-3' [SEQ ID NO:4]) primer pair. Following gel electrophoresis, the differential expressed gene fragments displayed by autoradiography.

The present invention is predicated in part on the use of techniques to identify differentially expressed genetic sequences between cancerous tissue and corresponding or "matched" normal tissue. The identification of genetic sequences differentially expressed, that is, up- or down-regulated in cancer cells relative to the normal cells provides a useful diagnostic aid.

Accordingly, one aspect of the present invention provides a method for detecting a molecular marker associated with normal or abnormal tissue from a mammal, said method comprising isolating total RNA from said abnormal tissue and corresponding tissue from a non-abnormal individual, generating complementary DNA molecules using reverse transcription-polymerase chain reaction (RT-PCR) and subjecting said DNA molecules to separation means such that the presence or absence or relative presence or absence of complementary DNA molecules can be detected from abnormal tissue relative to non-abnormal tissue wherein the presence or absence of a complementary DNA molecule in one type of tissue relative to another is indicative of a molecular marker associated with normal or abnormal tissue.

The term "molecular marker" is used in its broadest sense and includes genetic sequences, genetic loci, genes, telomerases, promoters and coding and non-coding regions. Preferably, the molecular marker is a gene. More particularly, the preferred molecular marker of the present invention is a gene which is expressed in either normal or abnormal tissue but not both. The term "expressed" includes substantial expression or substantial non-expression and further includes differential expression between one form of tissue relative to another form of similar or the same tissue.

Reference herein to "normal" or "abnormal" tissue is used in its broadest sense but most preferably includes non-cancerous tissue (normal tissue) and cancerous or pre-cancerous tissue (abnormal tissue). An abnormal tissue type includes tissue generally present in an individual with a disease condition associated with the presence of this abnormal tissue but is generally absent from individuals not suffering from the same or similar condition.

The present invention extends to all mammals such as humans, primates, livestock animals (e.g. sheep, cows, pigs, horses, donkeys, goats), companion animals (e.g. dogs, cats), laboratory test animals (e.g. rabbits, mice, guinea pigs, hamsters) and captured wild animals. Most preferably, the mammal is a human. Reference herein to an "individual" includes a human or other mammal.

The term "total RNA" is not to imply the presence of all RNA in a cell or individual but includes any preparation which comprises mRNA.

A "corresponding tissue" means a matched tissue sample. For example, biopsy samples are generally obtained from the cancer tissue of an individual and corresponding (i.e. matched) tissue samples are obtained from the anatomically equivalent region in an individual without the same or similar cancer.

The term "separation means" is used in its broadest sense and includes any means by which DNA molecules can be separated based on size, charge, length, complexity or a combination of some or all of the above. Preferably, the separation is by electrophoretic or chromatographic means and most preferably the separation is by electrophoretic means. Conveniently, the separation provides a visual record of complementary DNA molecules present or absent in normal tissue relative to abnormal tissue. Accordingly, generally, the complementary DNA, preparations are separated by electrophoretic or chromatographic means in a manner which permits a comparison of molecules present or absent in normal tissue relative to abnormal tissue. Gel electrophoresis is one particularly useful separation means with complementary DNA preparations being run in parallel lanes.

Although the present invention is most conveniently practiced by preparing complementary DNA for abnormal and normal tissue, a database of expected DNA in normal tissue can be prepared. The presence or absence of a particular species of complementary DNA can then be ascertained by comparing DNA separated by abnormal tissue with a "normal control".

In a particularly preferred embodiment, there is provided a method for identifying a molecular marker capable of distinguishing between a cancerous condition and a non-cancerous condition, said method comprising isolating total RNA from cancer tissue from an individual and from matched non-cancer tissue from another individual, generating complementary DNA molecules using RT-PCR and comparing said DNA molecules from said cancer and non-cancer tissue by gel electrophoresis wherein the presence or absence of a particular DNA species in cancer or non-cancer tissue relative to the other of non-cancer or cancer tissue, respectively is indicative of a molecular marker for said cancer.

In a most preferred embodiment, the cancer is cervical cancer or a related cancer. The present invention extends, however, to the use of the subject method to detect molecular markers for any cancer or tumour. Reference herein to a "cancer" or "tumor" includes reference to all sarcomas and carcinomas.

In a significant subset of cancers, large numbers of genes are altered in expression thereby leading to an abnormal phenotype. The altered expression patterns may facilitate initiation or progression of a neoplasm, subsequently resulting in invasive behaviour of the tumor. On the other hand, some alteration of gene expression may be the result of tumorigenesis. The former provides crucial information concerning the molecular mechanism(s) leading to cancer, while the latter may serve as markers for specific steps occurring in this process.

Figure 3:
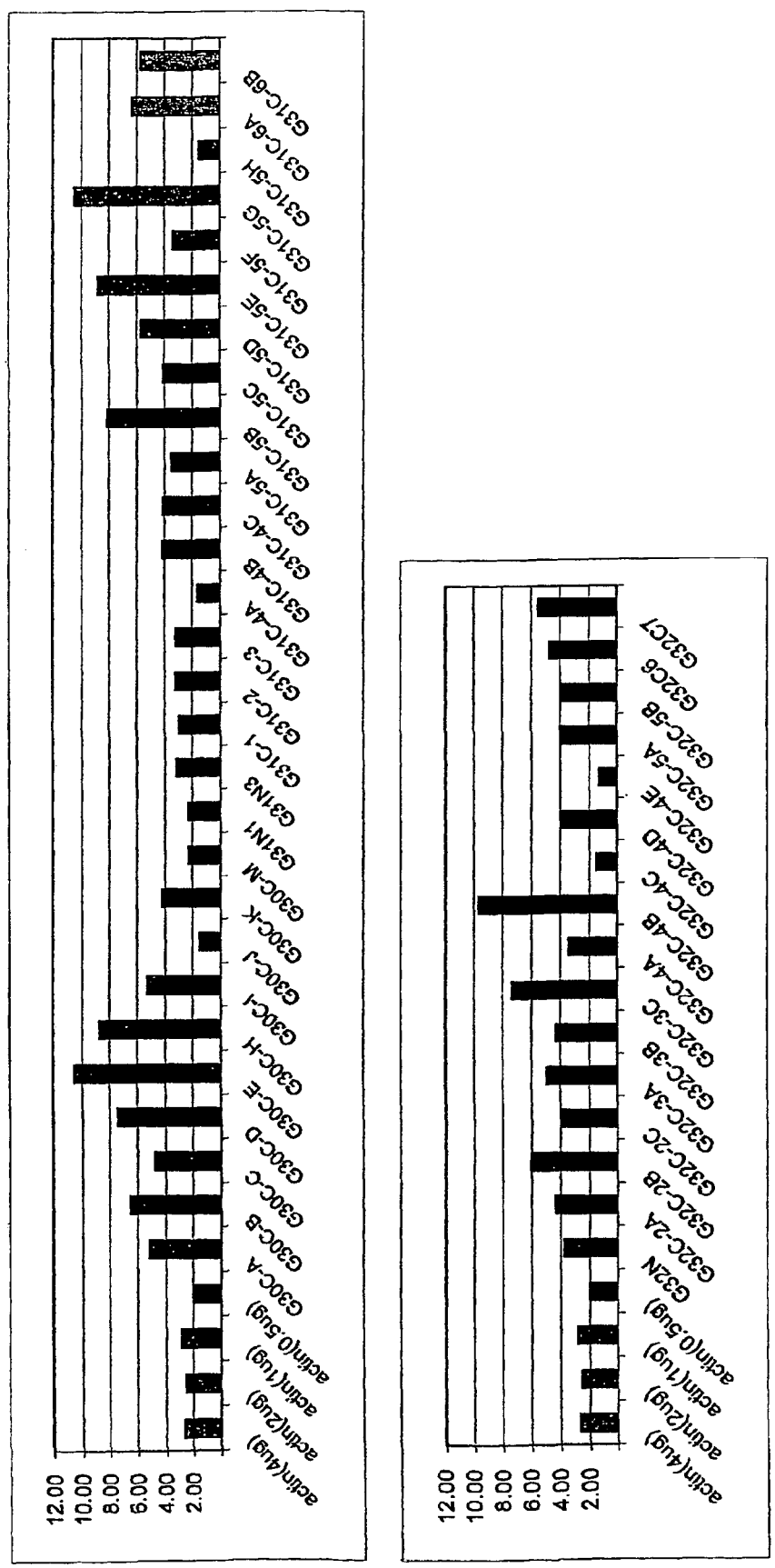
FIG. 3 is a photographic representation showing quantitative analysis of reverse Northern blot. Hybridization reactivity of reverse Northern blot was detected by PhosphorImager. The fold increase in hybridization reactivity with the cDNA probe derived from the cancer biopsy compared to that of the corresponding cDNA probe derived from normal tissue were demonstrated. 28 clones showed significantly up-regulated in cancer tissue.

In accordance with the present invention, using differential display techniques, the fingerprints of cDNA fragments amplified from cancer biopsies taken at different stages together with cDNA from matched normal tissue were displayed in the same gel to define specific diagnostic alterations between cervical cancer biopsies and normal tissue. cDNA fragments (Table 1) were cloned from RT-PCR differential display with primers. Based on reverse Northern blot analysis, the expression of 28 clones were confirmed to be significantly increased in the cancer biopsies with net fold increase ranging from 1.7 to 4.3 (FIG. 3). Among the amplified genes, eleven of the clones identified could be associated with energy consumption (G32C3B and G32C4B); signal transudation (G30CI and G31C6A); transcription regulation (G32C2B); translation (G30CA and G30CC); biosynthesis (G32C7, and G31C5E); and cellular metabolism (G30CD and G32C6) (Table 1).

Eleven of the 28 clones, viz. G30CE, G30CK, G31C4C, G31C5B, G31C5C, G31C5D, G31C5G, G32C2A, G32C3C, G32C4D and G32C5A appear to be novel gene sequences as they did not match to any the reported gene sequence in the GeneBank or EST databases (Table 1).

Figure 5:
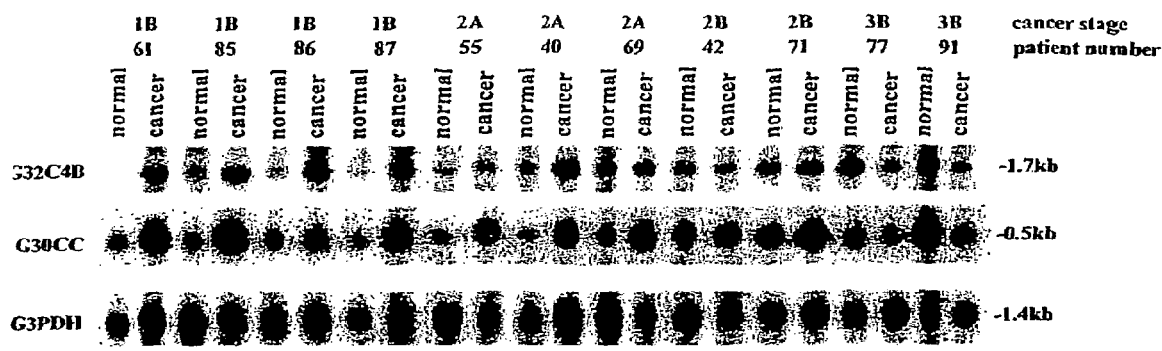
FIG. 5 is a photographic representation showing Northern blot analysis of clones G30CC and G32C4B in different FIGO stages of human cervical squamous cell carcinoma. Twenty mg of total RNA obtained from cancer biopsies of different FIGO stages and their corresponding adjacent normal epithelium were employed for Northern blot hybridization. G3PDH was employed as an internal control to normalize the amount of RNA.
Figure 7:
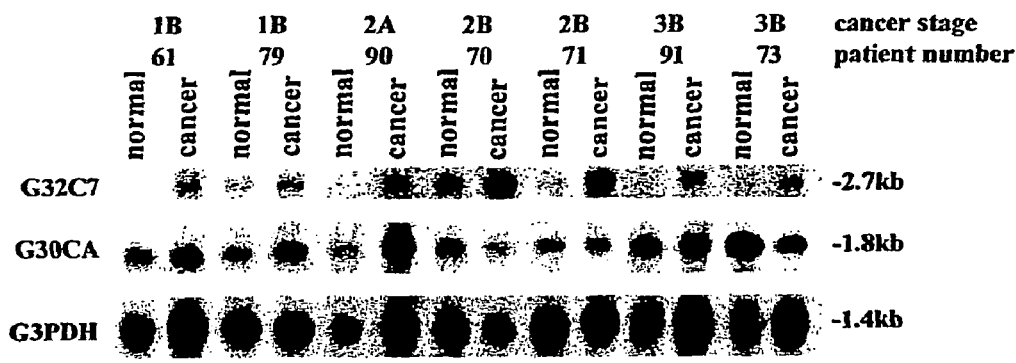
FIG. 7 is a photographic representation showing Northern blot analysis of clone G30CA and clone G32C7 expression in human cervical biopsies. Twenty μg of total RNAs obtained from human cervical cancer biopsies of different FIGO stages and their adjacent normal tissues were employed for Northern bolt hybridization. G3PDH was employed as an internal control to normalize the amount of RNA. The net fold increase in gene expression was determined following exposure of the membranes and quantitation by densitometric scanning using the BioRad FX PhosphorImager (BioRad, Richmond, Calif.).
Figure 8:
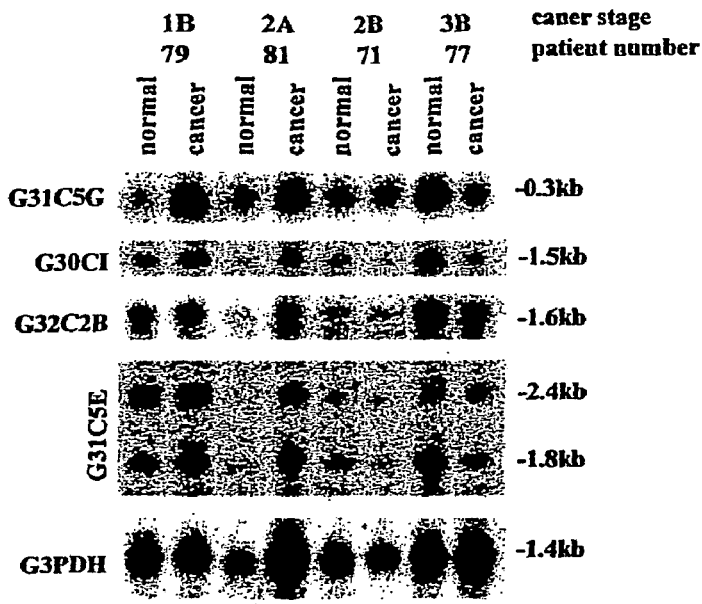
FIG. 8 is a photographic representation showing Northern blot analysis of clone G31C5G, clone G31CI and clone G32C2B expression in human cervical biopsies. Twenty μg of total RNAs obtained from human cervical cancer biopsies of different FIGO stages and their adjacent normal tissues were employed for Northern bolt hybridization. G3PDH was employed as an internal control to normalize the amount of RNA. The net fold increase in gene expression was determined following exposure of the membranes and quantitation by densitometric scanning using the BioRad FX PhosphorImager (BioRad, Richmond, Calif.).

Northern blot analysis indicated that seven particular genes, designated herein are "G30CA", "G30CC", "631C5G", "G32C4B", "G30CI", "G32C2B" and "G32C7" involved in early stage development of cervical carcinoma (FIGS. 5, 7-8).

Figure 9:
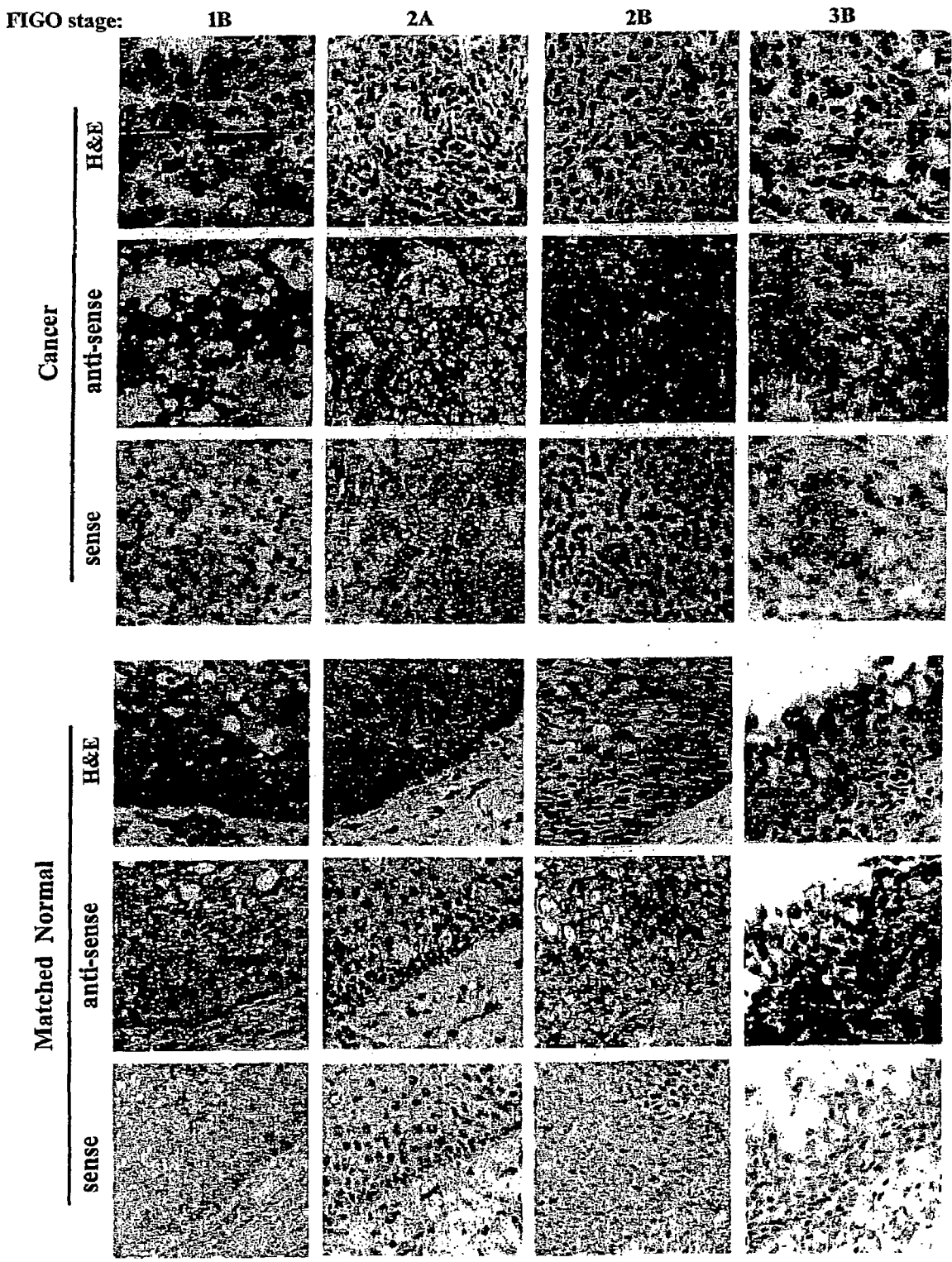
FIG. 9 is a photographic representation showing RNA-RNA in situ hybridization for G32C4B. Tissue sections of 10 μm thickness were prepared from human cervical cancer biopsies of different FIGO stages (1B, 2A, 2B and 3B), as well as the adjacent normal tissue. Consecutive tissue sections were either hybridized with DIG-labeled anti-sense or sense probe derived from clone G32C4B. Hematoxylin and Eosin staining was employed for histological identification. The magnification shown was 600×.
Figure 10:
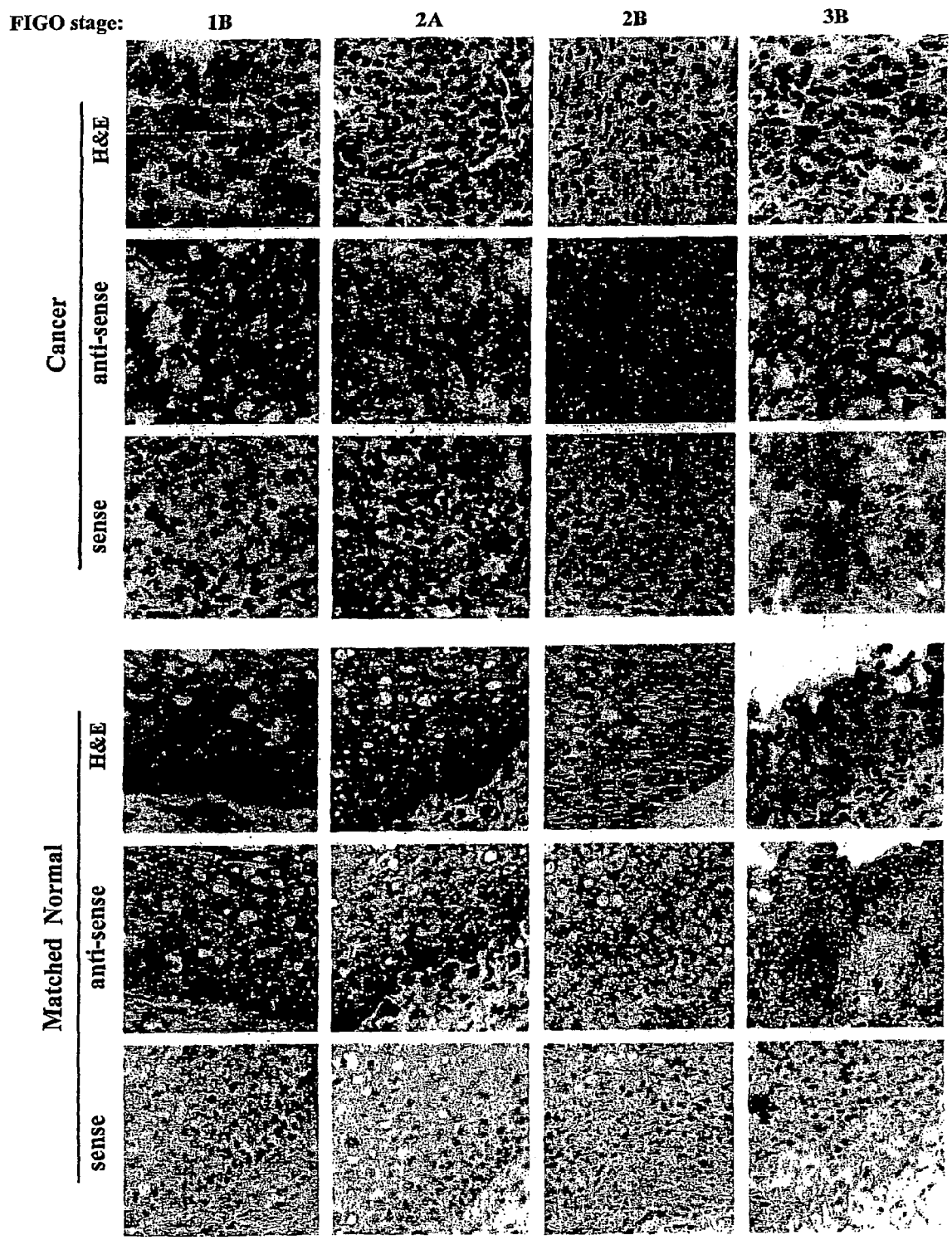
FIG. 10 is a photographic representation showing RNA-RNA in situ hybridization for G30CC. Tissue sections of 10 μm thickness were prepared from human cervical cancer biopsies of different FIGO stages (1B, 2A, 2B and 3B), as well as the adjacent normal tissue. Consecutive tissue sections were either hybridized with DIG-labeled anti-sense or sense probe derived from clone G30CC. Hematoxylin and Eosin staining was employed for histological identification. The magnification shown was 600×.

Of particular interest, two of these genes, namely G32C4B and G30CC, have been identified to be the NADH dehydrogenase 4 gene and the gene that encodes ribosomal protein S12, respectively. The over-expression of these two genes in cancer biopsies obtained from early invasive cell lesion of the uterine cervix indicates that these two genes are involved in the pathogenesis of human cervical neoplasia (FIG. 6). Most importantly, it was observed that, besides cancer lesions, the expression of G32C4B and G30CC could be detected in adjacent presumably histologically normal cervical tissues. The NADH dehydrogenase 4 and the ribosomal protein S12 genes can therefore provide significant value as an early diagnostic marker for human cervical cancer and to define a molecular margin for progressive disease (FIGS. 9 and 10).

Accordingly, another aspect of the present invention provides a genetic sequence comprising a sequence of nucleotides, which is expressed differentially in cervical cancer cells relative to matched normal cervical epithelial cells (Table 2).

The present invention extends to these sequences as well as derivatives thereof. A derivative is a genetic sequence comprising a single or multiple amino acid substitution, addition and/or deletion relative to a sequence referred to in Table 1.

Although the present invention is most conveniently practised by detecting differentially expressed nucleotide sequences, the instant invention extends to translation products and in particular peptides, polypeptides and proteins encoded by the differentially expressed nucleotide sequences. The differential expression as determined by the presence or absence of particular translation products is also a useful way of screening for molecular markers of normal or abnormal tissue. Accordingly, the present invention further extends to antibodies to the differentially expressed molecular markers associated with normal or abnormal tissue. Antibodies and in particular monoclonal antibodies are useful inter alia in immunoassays to screen for the presence of a differentially expressed product and may also be useful in immunotherapy.

The use of monoclonal antibodies in an immunoassay and in immunotherapy is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Douillard and Hoffman, Kohler and Milstein, 1975; 1976).

Another aspect of the present invention contemplates a method for detecting a molecular marker associated with normal or abnormal tissue in a biological sample from a subject, said method comprising contacting said biological sample with an antibody specific for said molecular marker or its derivatives or homologs for a time and under conditions sufficient for an antibody-molecular marker complex to form, and then detecting said complex.

The presence of the molecular marker may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control ample containing known amounts of molecular marker. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain a molecular marker including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In a typical forward sandwich assay, a first antibody having specificity for the molecular marker or antigenic parts thereof, is either covalently or passively bound to a solid surface.

The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g. from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the molecular marker. The second antibody is linked to a reporter molecule which is used to indicate the binding of the second antibody to the molecular marker.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody.

Alternatively, a second labelled antibody, specific to the first antibody is exposed to the target-first antibody complex to form a target-first antibody-second antibody tertiary complex. The complex is detected by the signal emitted by the reporter molecule.

By "reporter molecule", as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, -galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of molecular marker which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescene and EIA techniques are both very well established in the art and are particularly preferred for the present method. However, other reporter molecules, such as radioisotope, chemiluminescent or bioluminescent molecules, may also be employed.

The antibodies according to this aspect of the invention may also be used in immunotherapy such as but not limited to acting as antagonists for abnormal tissue associated with translation products. For example, where a translation product is a protein which facilitates the formation of abnormal tissue such as cervical cancer tissue, the administration of an antibody directed to the translation product may be useful in preventing its function associated with abnormal tissue development.

Accordingly, another aspect of the present invention contemplates a method for the treatment of an individual with abnormal tissue, said method comprising administering an immuno-interactive molecule directed to a molecular marker associated with the development of said abnormal tissue for a time and under conditions sufficient for the function of the molecular marker to be impaired thus reducing its ability to facilitate abnormal tissue development.

Preferably, the abnormal tissue is cervical cancer tissue.

Preferably, the molecular marker is a peptide, polypeptide or protein.

This aspect of the invention may alternatively be practised by the administration of a genetic molecule and reducing expression of the molecular marker. Examples of suitable genetic molecules include inter alia antisense molecules, ribozymes or sense molecules for co-suppression.

The present invention is further described by the following non-limiting Examples.

EXAMPLE 1

Tissue Collection and RNA Isolation

Biopsies were collected from patients with squamous carcinoma of the cervix. Punch biopsies with tischler forceps were taken from the tumor lesion for histo-pathological assessment as well as for RNA analysis. For histo-pathological analysis, the tissues were fixed in 10% buffered formalin and processed into paraffin blocks. Multiple step sections were made and stained with hematoxylin and eosin. Where indicated, PAS with and without diastase digestion and mucicarmine stains were performed. Tissues collected for RNA analysis were snapped frozen in liquid nitrogen. Wherever possible, normal cervical tissues far away from the tumor areas were taken for controls. The staging of cancer was done according to recommendations by the International Federation of Obstetrics and Gynacology (FIGO) [FIGO News, 1987). To avoid repetition in evaluating gene expression in the same patient, different patients were included in different studies. In total, 38 cervical cancer patients in various stages of the disease and five non-cervical cancer patients were studied. For all experiments, total cellular RNA was isolated using TRIzol Reagent (Gibco, BRL, Life Technologies, Grand Island, N.Y.) according to the manufacturer's manual and stored at −80° C. before being employed in experiments.

EXAMPLE 2

RT-PCR Differential Display

Total RNA was isolated from normal and cervical cancer biopsies and samples were treated with RNase-free DNase I (Promega, Madison, Wis.) to remove potential chromosomal DNA contamination. About 1 µg each of total RNAs from normal and cancer biopsies were used for reverse transcription.

First-strand cDNAs were synthesized by using an one-base anchored oligo-dT P21 as primer, amplified in parallel PCRs in the presence of [α-$^{33}$P]dATP by using 3 combinations of P30, P31 or P32 primers individually. The PCR cycling parameters were as follows: 40 cycles of 94° C. for, 30 sec, 40° C. for 2 min and 72° C. for 30 sec, followed by 72° C. for 10 min. The PCR products together with size markers were then separated on a 5.7% w/v denaturing polyacrylamide gel containing 7 M urea. The sequencing gel was run to resolve cDNA fragments sized from 150 bp to 1000 bp. Differentially expressed bands were cut out of the gel and cDNA fragments eluted by boiling the gel pieces in 100 µl H$_2$O for 15 min and were then used as templates for PCR re-amplification using the same condition as described above. A portion of the re-amplified PCR product was analyzed on a 2% w/v agarose gel to check the efficiency of re-amplification and to confirm the size of cDNA fragments. All PCR primers employed for reverse transcription and PCR were obtained from Gibco BRL (Life Technologies, Grand Island, N.Y.). Primers used included: P21 3'-GTTTTTTTTTTTCGAA-5'(SEQ ID NO:1); P30 5'-AAGCTTGG TGACA-3'(SEQ ID NO:2); P31 5'-AAGCTTAGTCAAG-3'(SEQ ID NO:3); P32 5'-AAGCTTCCACAGC-3'(SEQ ID NO:3). AmpliTaq DNA polymerase was purchased from Perkin-Elmer Corp. (Norwalk, Conn.). [α-$^{33}$P]dATP (2000 Ci/mmole) was obtained from New England Nuclear (Boston, Mass.). Denaturing polyacrylamide gel (5.7% w/v) containing 7 M urea was made using Gel-Mix 6 (Gibco BRL, Life Technologies, Grand Island, N.Y.).

EXAMPLE 2 cDNA Cloning and Sequencing

Re-amplified cDNA fragments were cloned into either the pCR2.1 vector using the TA cloning system from Invitrogen (San Diego, Calif.) or the pCR-TRAP Vector from GenHunter (GenHunter Corp. Nashville, Tenn.). DNA sequencing was performed either using Sequenase Kit Version 2.0 (United States Biochemical, Cleveland, Ohio), or by automated sequencing using ABI Prism 377 DNA Sequencer (Perk-in-Elmer Corp., Norwalk, Conn.). The nucleotide sequences obtained were analyzed by BLAST search (National Centre for Biotechnology Information).

EXAMPLE 3 cDNA Microarray Fabrication and Hybridization cDNA clones were amplified in 100 µl PCR reactions, 5 µl PCR product was analyzed on a 2% w/v agarose gel after which the remaining PCR products were purified by isopropanol precipitation, resuspended in 15 µl 3×SSC and printed onto poly-L-lysine (Sigma Microsystems Inc., Woburn, Mass.). Housekeeping genes including G3PDH, β-actin, β-2-microglobulin, α-tubulin, cyclophilin and ubiquitin were also spotted as internal controls for normalization. Each slide was hydrated for 2-3 sec over a steaming 100° C. water-bath, snap-dried for 5 sec on a 100° C. heating block and crosslinked with 550 mJ ultraviolet irradiation using a Stratalinker (Stratagene, LaJolla, Calif.). The slide was then washed for 10 min in 0.2% w/v SDS and rinsed 5× in distilled water before being denatured for 5 min in 100° C. distilled water, desiccated for 5 min in 95% v/v ethanol and air-dried for 5 min in an 80° C. oven.

Comparative hybridizations were carried out using cDNA reversetranscribed from total RNA isolated from tumor biopsies and matched adjacent normal tissue of 10 individual cervical cancer patients in varying stages of disease. Total RNA was reverse-transcribed into cDNA, labelled with Cy3 (for tumor cDNA) and Cy5 (normal cDNA) fluorescent dyes and hybridized onto the slides according to the 3DNA (trade mark) Expression Array Detection Kit protocol recommendations (Genisphere Inc., Montvale, N.J.). Labelled cDNA from cancer and normal tissues were hybridized simultaneously onto a single glass slide in 10 separate hybridizations. Humidified microarray hybridization cassettes were used to contain all slides during hybridization incubations (TeleChem International Inc., Sunnyvale, Calif.). Hybridized microarrays were scanned using a GMS 418 laser scanner (Genetic Microsystems Inc, Woburn, Mass.). Separate images were acquired for Cy3 and Cy5. The signal and background signals were then quantified with Imagene 3.0 quantification software (BioDiscovery Inc., Los Angeles, Calif.). Generated signal values were analyzed and visualized using Cluster and Treeview programs (M. Eisen, University of California, Berkeley; See (rana.lbl.gov).

Signals were measured as the mean pixel intensity within each circumscribed spot and background was measured using the mean pixel intensity outside the circumscribed spot diameter within a specific square location. Spots which were contaminated with fluorescent specks or other blemishes, or where background values were higher than the spot signal were considered as missing. The signal intensities from both Cy3 and Cy5 channels were normalized by applying a single scaling factor computed by taking the ratio of the total signal intensities of each channel such that the signal intensities of internal controls on each array would have a Cy3/Cy5 ratio of 1.0. Spots that gave signals of 2.5-fold or more difference in comparison to the normal controls would be considered as differentially expressed.

EXAMPLE 4

Reverse Northern Blot

Two µg gene fragment from each clone, as well as different amount of α-actin (0.5, 1, 2, or 4 µg) were blotted on a Hybond-N$^+$ nylon transfer membrane (Amersham, Piscataway, N.J.) using a slot-blot apparatus, while α-actin was used as an internal control. After 5 min denaturation at room temperature with 1.5 M NaCl, 0.5 M NaOH, and 5 min neutralization at room temperature with 1.5 M NaCl, 1 M Tris-HCl pH 7.4, the DNA was fixed to the membrane by incubation at 80° C. for 2 hr. $^{32}$P-labeled cDNA probes were prepared by reverse transcription with 30 µg total RNA isolated either from pooled tumor biopsies from six patients or from their matched normal biopsies. The reaction was performed by incubation at 42° C. for 1 h in the presence of 1000 U SuperScript™ (trade mark) II reverse transcriptase (GibcoBRL, Life Technologies, Grand Island, N.Y.), with 5 µM Oligo(dT)$_{16}$ primer (Perkin-Elmer Corp. Norwalk, Conn.), 10 mM DTT, 0.1 mM dGTP/dTTP mix, 60 µCi [α-$^{32}$P]dATP and [α-$^{32}$P]dCTP (3000 Ci/mmol, NEN, Boston, Mass.). RNAs were then hydrolyzed by a 30 min incubation at 65° C. with 9 µl 3 N NaOH in 70 µl reaction volume, and followed by neutralization with adding 30 µl 1 M Tris-HCl (pH 7.4), 9 µl 2 N HCl and 22 µl H$_2$O. Unincorporated nucleotides were removed by NucTrap probe Purification Columns (Stratagene, LaJolla, Calif.). Hybridization was performed at 40° C. with either normal or cancer cDNA probe at 4×10$^6$ cpm/ml in presence of sheared salmon sperm DNA (Sigma, Mo.). The net fold increase was calculated as the ratio gene expression obtained with the probe derived from RNA of cancerous tissue over the level obtained from RNA of normal tissues after normalization with α-actin.

EXAMPLE 5

Northern Blot Analysis

Twenty µg of total RNA isolated from cancer biopsies or their adjacent histo-pathologically normal tissues were employed for Northern blot analysis. After electrophoresis, the RNA was transferred to Hybond-N$^+$ nylon transfer membrane (Amersham, Piscataway, N.J.) and probed with random hexa-nucleotide-primed $^{32}$P-labeled cDNAs clones using high prime DNA labeling kit (Boehringer Mannheim GmbH, Mannheim, Germany). Unincorporated nucleotides were removed by NucTrap probe Purification Columns (Stratagene, LaJolla, Calif.). Hybridization and washes were performed as described previously (Soong, et al., 1992). Hybridization to the housekeeping gene G3PDH cDNA probe (Clontech Laboratories Inc., Palo Alto, Calif.) was used to quantitate the loading of RNA. After hybridization and washing, the membranes were exposed. For analysis, the radioactivity associated with each band was quantitated by densitometric scanning using the BioRad, Richmond, Calif.).

EXAMPLE 6

PhosphorImager Analysis

After hybridization and washing, the membranes were exposed. For analysis, the radioactivity associates with each band was quantitated by densitometric scanning using the BioRad FX PhosphorImager (BioRad, Richmond, Calif.)

EXAMPLE 7

RNA-RNA in Situ Hybridization

The RNA-RNA in situ hybridization was performed by DIG (digoxigenin)-labeled cRNA probe using DIG RNA labeling Kit (Boehringer Mannheim GmbH, Mannheim, Germany). Two sub-clones with opposite orientation of the gene fragment insert were selected further to produce sense and anti-sense probe. The labeling reaction was carried out according to the manufacturer's protocol using DIG RNA labeling Kit. After linearization of the template DNA at BamH1 site, 75 U of T7 RNA polymerases were used in the presence of DIG-UTP to synthesis DIG-labeled transcripts.

The cancer biopsies and their matched normal tissue were collected from the patients in different cancer stages. Biopsies were cut into 10 µm thick frozen section and were mounted directly on the microscope slides. The tissue sections were fixed by incubating at 50° C. for 2 min, at room temperature for 30 min, and a subsequently incubation at room temperature with PBS containing 4% v/v paraformaldehyde for 7 min, then for 3 min with PBS followed by 2 washes with 2×SSC for 5 min each. The pre-hybridization was performed by incubating at 37° C. for 1 hr in block solution containing 5% w/v skim milk powder, 4×SSPE, 50% v/v deionized formamide, 30 µg herring sperm DNA, 1% w/v SDS and DEPC-treated H$_2$O. 200 ng/ml of DIG-labeled anti-sense cRNA probe or sense cRNA probe were then incubated with tissue section at 37° C. overnight in hybridization buffer (16.6% w/v dextran sulfate, 5% w/v skim milk powder, 4×SSPE, 50% v/v deionized formamide, 1% w/v SDS and DEPC-treated H$_2$O). The slides were subsequently washed twice with 2×SSC at room temperature for 5 min. The tissue sections were incubated at room temperature for 2 hr with 100 mM Tris-HCl pH 7.5 and 150 mM NaCl buffer containing 1% w/v BSA and 0.5% w/v α-alkaline phosphatase-conjugated anti-DIG antibody (BM, MannLein, Germany). For the colour development, the tissue section slides were soaked 0.1 M Tris-HCl pH 9.5, 0.1 M NaCl, 0.05 M MgCl$_2$, 3.4% NBT, 1.8% BCIP, 2.4% levamisole at room temperature overnight in the dark. The color reaction was stopped by incubating the slides in 10 mM Tris-HCl pH 8 and 1 mM EDTA at room temperature for 5 min and soaked in H$_2$O for 5 min at room temperature. ollowing counter-staining staining in Hematoxylin (BDH Laboratory Supplies, Dorset, England) for 2-5 sec, the tissue section slides were washed with H$_2$O at room temperature and mounted with coverslps in Kaiser's glycerol gelatin solution (Merk KgaA, Darmstadt, Germany).

For the hematoxylin and eosin staining, tissue sections were soaked in hematoxylin (filtered hematoxylin contains 1 ml acetic acid v/v) for 4 min and washed in H$_2$O, followed by dipping into 0.5% v/v acid alcohol (0.5% v/v HCl in 75% v/v alcohol) for 2 sec and subsequently washed in H$_2$O. Tissue sections were then soaked in eosin solution (1% v/v eosin stock solution: 70% alcohol=1:3) for 3 min and washed by running H$_2$O. Slides were viewed with the Olympus BX 60 microscope (Olympus Optical Co. Ltd).

EXAMPLE 8

Identification of Differentially Displayed cDNA Fragments from Human Cervical Cancer Biopsies cDNA were reverse transcribed using total RNA isolated from six biopsies obtained from patients with squamous cell carcinoma of the cervix of different FIGO stages. RNA isolated from the corresponding adjacent histo-pathologically normal epithelial tissues were similarly amplified and their gene expression profiles compared in order to identify tumor-specific alterations (FIG. 1). Cervical cancer biopsies of different FIGO stages were utilized in order to avoid isolating "false positive" differentially displayed cDNA fragments from a specific type of tumor biopsy (Liang et al., 1994). The inventors hypothesized that true differentially displayed bands that are important for carcinogenesis should be generally up-regulated or down-regulated in most, if not all, cervical cancer samples when compared to the adjacent normal samples and that these bands should be reproducibly generated by differential display analysis. To ensure reproducibility, all PCR reactions including the RT reactions were performed in triplicates and each PCR product was applied in different electrophoretic separation in denaturing polyacrylamide gels with different running time. The patterns of amplified PCR products from six independent samples of mRNAs from cancer biopsies or matched histo-pathologically normal tissues showed comparable identical banding patterns for each of the primer sets employed (FIG. 1).

In general, it was observed that the majority of the PCR bands generated from the cancer biopsies showed higher intensity than their corresponding normal counterparts (FIG. 1). With the three primer sets P21-P30, P21-P31 or P21-P32 tested. Eighteen bands were demonstrated to be distinctly different between the cDNA bands generated from mRNAs of cancer biopsies and the corresponding matched normal control tissues (FIG. 1). Fourteen of these 18 bands were found to be up-regulated in the cancer biopsies and four bands (G31N1, G31N2, G31N3 and G32CN) were down-regulated (FIG. 1). Seventeen of the 18 bands were successfully extracted from the acrylamide gels, reamplified and cloned individually into either pCR-TRAP or pCR2.1 vectors. A total of 44 clones were identified. Gene fragments from G31N1 and G31N2 were considered as the same gene as they had identical sequences. All cloned cDNA fragments were subsequently sequenced and their sizes were found to be between 176 to 425 bp in length (Table 1). All clones were confirmed to have the expected primer sequences at their respective 5' and 3' ends upon sequencing. The inventors have also employed a pooled RNA sample obtained by pooling the RNA samples from the six patients that were employed for differential display for reverse Northern blot analysis. This was to confirm the clones which expression were up-regulated as detected by the differential display study (FIG. 1). The result obtained with this analysis was by and large comparable to that obtained via cDNA microarray analysis (FIG. 2).

To confirm that the expression of these 44 isolated clones was amplified in human cervical cancer, reverse Northern blot analyses were performed. Of the 44 cDNA clones isolated, the expression of 28 clones were confirmed to be significantly increased in the cancer biopsies with net fold increase ranging from 1.7 to 4.3 (FIGS. 2 and 3). The sequences of these 28 clones are listed in Table 2. From the differential display studies, it was observed that the expression of clones G31N1, G31N3, and G32N were higher in normal tissues in comparison to cancer tissues (FIG. 1). However, this observation could not confirmed with the reverse Northern blot analysis (FIG. 2) and the inventors have, therefore, regarded these three clones to be false positives.

EXAMPLE 9

Profile of Gene Expression of the cDNA Clones in Different FIGO Stages

To study the potential role of the 44 cDNA clones in the pathogenesis of human cervical cancer, the gene expression profile of these 44 clones in 10 cervical carcinoma biopsies were compared with their corresponding adjacent normal tissues using cDNA microarrays. cDNA microarrays were generated by printing the DNA purified from the 44 cDNA clones in duplicates onto coated glass slides. Among the 10 pairs of tissue biopsies studied, three pairs were obtained from stage 1B cancer patients, two from stage 2A and stage 2B and three from stage 3B.

Results obtained from the cDNA analyses demonstrated u-regulated expression of 25 of the 44 clones in all 10 cervical cancer patients (FIG. 2).

The inventors reasoned that for a gene to be potentially employed as a diagnostic marker, its RNA should be in abundance. Twenty-two of the 25 clones that have been confirmed to be up-regulated by microarray analysis were employed as probes for Northern blot analysis with RNA isolated from the four cervical cancer cell lines, HeLa, CaSKi, SiHa and HT-3. Nine of the clones demonstrated a strong hybridization signal. They were then chosen as probes for subsequent Northern blot analyses of RNA purified from human cervical squamous cell carcinoma biopsies of various FIGO stages and that of adjacent normal epithelium. It was observed that two of the clones, namely G30CC and G32C4B, showed elevated levels of expression in cervical cancer biopsies of early FIGO stages (FIG. 5). In comparison to adjacent histo-pathological normal epithelium, the expression of clone G30CC was up-regulated by approximately 5-fold in stage 2A cancer tissues while G32C4B was also up-regulated by a similar magnitude in stage 1B cancer tissues. The expression of these two clones were apparently also elevated in the adjacent histo-pathologically normal epithelium collected from the late FIGO stage patients (FIG. 5).

Late cervical cancer tissues would include patients of FIGO stages 2B and 3B and in whom the carcinoma extends beyond the cervix with obvious parametrial involvment (FIGO News, 1987).

To study the identity of clones G32C4B and G30CC, the inventors employed these clones as probes for the isolation of the corresponding full-length cDNA genes by screening a cDNA library derived from the HeLa human cervical cancer cell line. Using ClonCapture cDNA Selection Kit, representative positive clones were isolated from the HeLa cDNA library using G32C4B or G30CC as probes. The cDNA obtained were sequenced and they were found to be homologous to the reported NADH dehydrogenase subunit 4 gene and the ribosomal protein S12 mRNA, respectively.

EXAMPLE 10

Sequence Analysis

Through the BLASTN sequence search (National Centre for Biotechnology Information), it was determined that 28 of the 44 cloned cDNA fragments are either homologous to previously reported genes in the Genebank or to expressed sequence tags (EST) (Table 1). It was found that the cDNA sequences of G30CC, G30CD, G30CI, G30CJ, G31C5H, G32C3B, G32C4B and G32C7 were located within the coding region of the reported gene sequence and that the sequences of clones G31C4B and G32C2C were in the reverse orientation with respect to the reported homologous sequence. The sequences for clones G30CB and G31C6B were also found to be in the reverse orientation in relationship to the reported sequences of two isolated EST clones. Eleven of the 28 clones, viz. G30CE, G30CK, G31C4C, G31C5B, G31C5C, G31C5D, G31C5G, G32C2A, G32C3C, G32C4D and G32C5A appear to be novel gene sequences as they did not match to any the reported gene sequence in the GeneBank or EST databases (Table 1).

When the sequences of clones G32C4B and G30CC were blasted to the GeneBank for homology search, the search results showed that clone G32C4B was homologous to the reported NADH dehydrogenase subunit 4 gene with 100% identity (Table 1). On the other hand, clone G30CC was homologous to the ribosomal protein S12 mRNA with 99% identity (Table 1).

To further confirm the identity of clones G32C4B and G30CC, the inventors employed clones G32C4B and G30CC as probes to isolate the corresponding full-length cDNA genes by screening a cDNA library derived from the human Hela cell line. Representative positive clones, obtained using ClonCapture cDNA Selection Kit, from the Hela cDNA library with either G32C4B or G30CC as probes were sequenced and again found to be homologous to the NADH dehydrogenase subunit 4 gene and the ribosomal protein S12 mRNA respectively. The full-length cDNA clones obtained were then employed as probes for Northern blot analyses and the results were similar to those obtained with G32C4B or G30CC (FIGS. 4 and 6).

EXAMPLE 11

Expression of the Cloned cDNA Fragments in Different FIGO Stages of Human Cervical Cancer To study the potential role of the newly isolated cDNA in the pathogenesis of human cervical cancer, the inventors employed the nine of the 28 isolated clones to probe mRNA purified from human cervical cancer biopsies of various pathological stages. Earlier studies by the inventors have shown that these nine clones gave strong hybridization signals with RNA purified from human cervical cancer cell lines.

mRNA from cervical cancer biopsies of FIGO stages 1B, 2A, 2B and 3B along with the matched normal tissue biopsies were isolated. It was observed that clone G32C4B expressed strongly in all the stage 1B human cervical cancer samples studied (FIG. 5). The level of expression of G32C4B was more than 5 times higher than that of the corresponding matched normal biopsies (FIG. 5). Interestingly, it appeared that the overall gene expression of clone G32C4B reduced in relationship to the matched normal tissues as disease progressed (FIG. 5). The expression of G32C4B was significantly reduced in cervical cancer at stage 2A (FIG. 5) and its expression in stages 2B and 3B human cervical cancers specimens were similar to that of the matched normal (FIG. 5). These results suggest that the expression of clone G32C4B peaked at the early onset of disease.

The expression of clone G30CC in stage 1B cervical cancer was approximately three folds over that of the matched normal biopsies (FIG. 5). This difference increased to approximately five folds for stage 2A cervical cancer in comparison to that of matched normal biopsies (FIG. 5). However, the level of expression of G30CC appeared to peak for stage 2A cervical cancer and it dropped to a level of expression comparable to that of the matched normal biopsies for cervical cancer tissues obtained from patients at later stages of disease (FIG. 5).

Similarly, the expression of clones G30CA, G32C7 and G31C5G was relatively high compared to the corresponding normal tissues for cervical cancer tissues obtained from patients with disease at early stages (FIGS. 7 and 8). However, when cervical cancer tissues obtained from late stages of diseases were studied, their level of expression was comparable to that of the corresponding matched normal tissues (FIGS. 7 and 8).

Clone G30CI only weakly hybridized to human cervical cancer biopsies obtained at various stages (FIG. 8). Clone G30CK failed to detect any expression in the cancer and normal tissue biopsies.

EXAMPLE 12

RNA-RNA in Situ Hybridization

The results obtained from the inventors' Northern blot analyses indicated that the expression of G32C4B and G30CC also elevated in the matched normal tissues collected together with the late clinical stages of cervical cancer biopsies. To explore the possible significance of G32C4B and G30CC amplification in the matched normal biopsies towards the late FIGO stages and the cell types involved, the inventors conducted RNA-RNA in situ hybridization study.

G32C4B and G30CC probes were synthesized in both the anti-sense and sense orientations as described in materials and methods and employed for in situ hybridization studies. Histological identification was carried out in consecutive sections following H&E staining of the sections. Cervical cancer biopsies of various FIGO stages were studied along with their matched normal tissues. Two patients for each of the FIGO stages were studied and the results of one representative patient were shown.

Strong hybridization signals for G32C4B and G30CC could be detected consistently in the cytoplasm of squamous carcinomas of FIGO stages 1B, 2A, 2B and 3B (FIGS. 9 and 10). In comparison, only weak hybridization signals could be detected in adjacent fibromuscular stroma cells for all the various stages of cervical cancer biopsies studied (FIGS. 9 and 10). No hybridization signal could be detected in the normal squamous cells of matched adjacent tissues obtained from stage 1B cervical cancer patients with the G32C4B anti-sense probe (FIG. 9). On the other hand, although no hybridization signal could be detected with the G32C4B probe in the para-epithelial cell layers, faintly positive hybridization signals could be detected within the basal and immature epithelial cell layers in the matched adjacent tissues obtained from stage 2A cervical cancer patients (FIG. 9). Similarly, the G30CC anti-sense probe did not hybridized to the para-epithelial cell layers in matched normal tissues obtained from both FIGO stages 1B and 2A cervical cancer patients, positive hybridization signals were detected within the basal immature epithelial cell layers (FIG. 10). More significantly, when the matched normal tissues obtained from FIGO stages 2B and 3B cervical cancer patients were studied with G32C4B and G30CC anti-sense probes, strong hybridization signals could be obtained in histologically normal epithelial cell layers (FIGS. 9 and 10). The hybridization signals were most intense in the basal immature epithelial cells (FIGS. 9 and 10).

EXAMPLE 13

Figure 11:
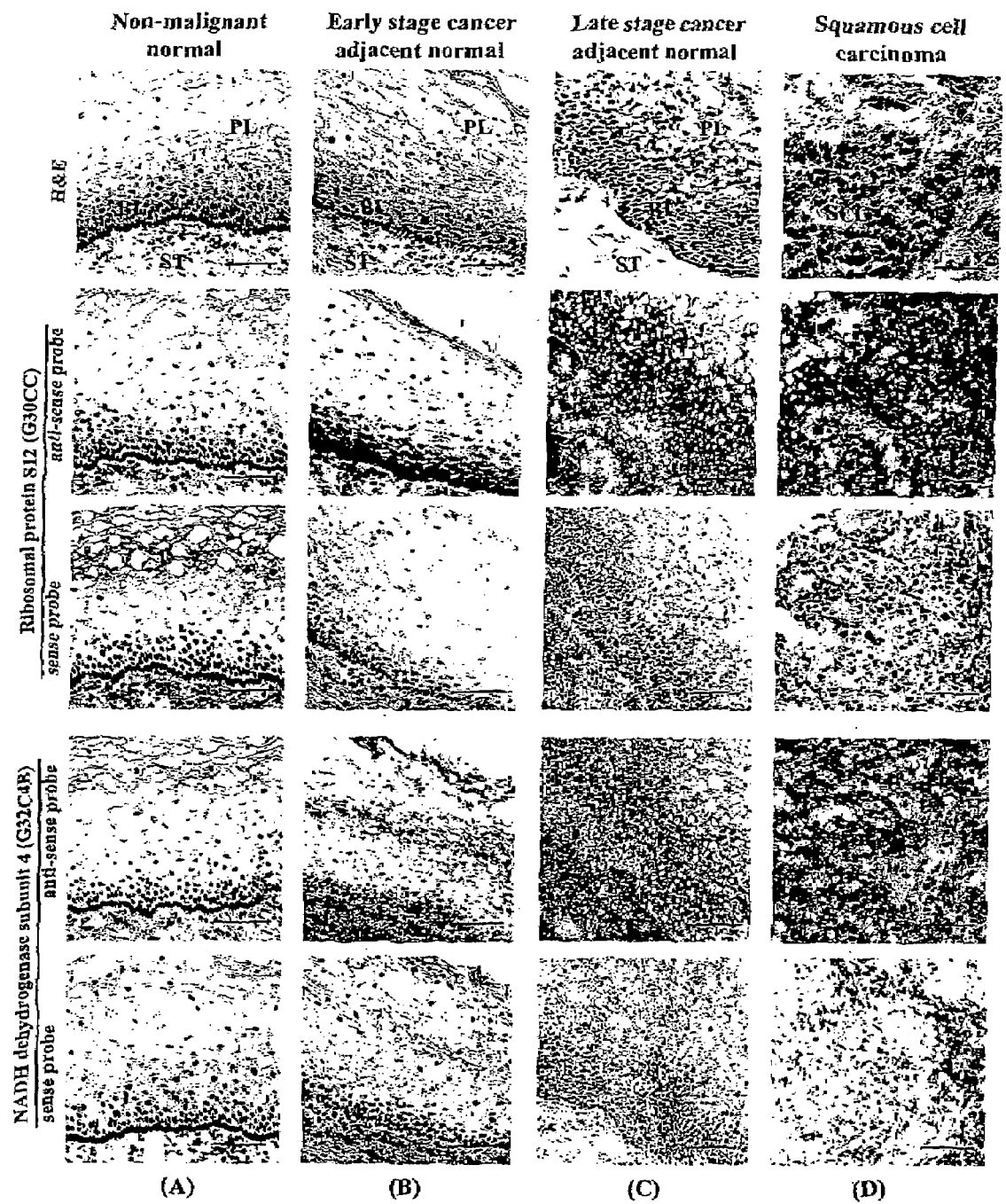
FIG. 11 is a photographic representation showing RNA-RNA in situ hybridization studies of clones G30CC and G32C4B with normal cervical squamous epithelium, cervical squamous cell carcinoma adjacent epithelium collected from early or late FIGO stages and squamous cell carcinoma biopsies. Consecutive tissue sections of 10 μm thickness were hybridized to DIG-labeled anti-sense or sense probe derived from clone G30CC or G32C4B. Hematoxylin and Eosin staining was employed for histology identification. Representative results obtained from clones G30CC and G32C4B to four different cervical tissue biopsies are presented. (A) Normal cervical squamous epithelium collected from non-malignant patient; (B) adjacent histo-pathological normal tissues obtained from an early stage cervical squamous cell carcinoma patient; (C) adjacent histo-pathological normal tissues obtained from a late stage cervical squamous cell carcinoma; and (D) a squamous cell biopsy section. The scale bar in the figures represents 80 μm. (BL, basal-layer epithelial cells; PL, par-layer epithelial cells; ST, stromal cells; SCC, squamous cell carcinoma.)

Level of Gene Expression of NADH Dehydrogenase Subunit 4 Gene and Ribosomal Protein S12 in Adjacent Normal Tissues of Cervical Cancer Tissues The results obtained from the inventors' Northern blot analysis indicated that the expression of NADH dehydrogenase 4 and the ribosomal protein S12 gene was also elevated in the adjacent normal epithelium collected together with the late clinical stages of cervical cancer biopsies. To confirm the possibility that the NADH dehydrogenase 4 gene and the ribosomal protein S12 gene are progressively up-regulated in cancer adjacent biopsies as the cancer progresses, as well as the cell types involved, the inventors conducted RNA-RNA in situ hybridization studies. Squamous cell cervical carcinoma biopsies of various FIGO stages, along with their corresponding adjacent normal tissues were employed for in situ hybridization. A total of 14 patients with squamous cell carcinoma of the cervix and their corresponding adjacent normal tissues were studied and representative results were shown in FIG. 11.

The up-regulated expression of the ribosomal protein S12 gene was detected within the basal immature epithelial cell layers (BL) in 10 out of 10 adjacent histo-pathological normal epithelium of early stage cervical cancer patients (eight patients of stage 1B and six patients of stage 2A) (FIG. 11B). No hybridization signal could be found in the para-layers epithelial cells (PL) in all of these tissue sections. Overall, only weak hybridization signals could be detected within the basal immature epithelial cell layers for the NADH dehydrogenase 4 gene in adjacent histo-pathological normal tissues of early stage cervical cancer patients (2 out of 10 patients) (FIG. 11B). As expected, NADH dehydrogenase 4 gene and the ribosomal protein S12 hybridized strongly to all stage cervical cancer tissues (FIG. 11D). In comparison, when the adjacent histo-pathologically normal tissues of late stage cervical cancer patients were studied, strong hybridization signals for the NADH dehydrogenase 4 gene and the ribosomal protein S12 gene were obtained in all the presumably histologically normal epithelial cell layers (4 out of 4 patients studied) (FIG. 11C). The hybridization signals were most intense in the basal immature epithelial cells (FIG. 11C). The negative control demonstrated that NADH dehydrogenase 4 gene and the ribosomal protein S12 gene did not hybridize to normal cervical epithelium obtained from patients who were admitted for surgery for non-malignant conditions (FIG. 11A).

EXAMPLE 14

Clinical Implication of Molecular Marker

CIN lesions are induced by persistent HPVs. The detection of high risk HPV infection has been proposed as a useful marker to diagnose cervical cancer. However, infection induced by high-risk HPV types is found in about 10% of healthy normal woman without clinical evidence of cervical lesions (Kjaer et al., 1997). Most high risk HPV infections usually last only for several months (Ho et al., 1998). The peak incidence of the disease occurs in women over 40 years of age; however, the peak incidence for HPV infection is in the 20s, therefore, there is a long latency period between the time of HPV infection and cancer appearance (Lazo, 1999). Therefore, an HPV-based screening program would both lead to over-investigation of many women and fail to identify a proportion of cases.

On the other hand, the vast majority of low-grade CIN lesions regress spontaneously, and only very few persist or progress to high-grade cervical dysplasia. Ostor (1993) reported that the approximate likelihood of regression of CIN 1 is 60%, persistence 30%, progression to CIN 3 10%, and progression to invasion 1%. The corresponding approximations for CIN 2 are 40%, 40%, 20%, and 5%, respectively. The likelihood of CIN 3 regressing is 33% and progressing to invasion greater than 12%. A later investigation, indicated that 11% of CIN I lesions on average progress to a higher grade dysplasia and the remainder either regress or persist (Duggan, 1998).

Treatment of cervical lesions is totally dependent on histopathologic judgment of whether or not a lesion is invasive. This distinction can be extremely difficult to assess, especially in small biopsy specimens and curettage material. A sensitive and objective diagnostic procedure determining the invasive potential of cervical neoplastic cells would, therefore, be of substantial value. Alternatively, despite the low risk for progression, currently all of the high-grade CIN lesions are removed by surgical resection (conization) to securely avoid the development of invasive carcinomas because there is no criterion that allows us to differentiate regressing or persisting lesion from those that will progress. Thus, the lack of progression marker results in a significant number of over treated women, whose lesions would have spontaneously cured. As morphology by itself does not predict which lesion will progress or regress, future efforts should seek factors other than morphological to determine the prognosis in individual patients.

Moreover, residual, recurrent, and persistent disease was most common in patients with incompletely excised CIN at ectocervical and endocervical margins and deep margins of resection than in patients with completely excised CIN (Zaitoun et al., 2000). One report suggested that despite extrafascial hysterectomy for presumed adenocarcinoma in situ (ACIS) of the cervix, a residual focus could remain and present later as invasive adenocarcinoma (Krivak et al., 2000). At long term follow up, patients with CIN who have residual disease are at increased risk of persistent disease and should, therefore, be followed up regularly. Since ACIS is not reliably diagnosed by cervical cytology and colposcopy, patients undergoing conservative management have been typically followed by endocervical curettage (ECC) in combination with Papanicolaou smear. Conversely, the ECC was positive in only 43% of patients with glandular lesions (Poynor et al., 1995). Hence, Pap smears in combination with ECC still inadequate for the detection of the recurrence of cervical adenocarcinoma.

Once cervical cancer is diagnosed, clinical staging takes place. Early-stage tumors can be managed with cone biopsy or simple hysterectomy. Higher stage tumors can be treated surgically or with radiotherapy. Advanced metastatic disease may respond to radiation therapy and concurrent chemotherapy. After these treatments, protein markers are needed for the detection of recurrence (Canavan et al., 2000).

Recurrent cervical carcinoma has very poor prognosis, mainly because there is no effective systemic therapy which would increase the duration of survival (Piamsomboon et al., 1996). 5-year survival rate of recurrent cervical cancer was only 5% (Burke et al., 1989). However, following radical hysterectomy for stage I-IIA cervical carcinoma, 10%-15% of women will have a recurrence. Sixty percent of these recurrences will be located in the pelvis alone (Lanciano, 1996). The mean time-to-recurrence was 21.7 months and greater proportions of patients were with adenocarcinoma, lymph-node metastasis, and involved surgical margins. Routine follow-up Pap smear seemed to be a poor indicator of disease status (Tay et al., 1997).

Therefore, a major problem in the diagnosis of patient with cancer is the lack of specific tumor markers, for early detection, for the accurate prediction of biological behavior and for accurate assessment of prognosis. Results by the inventors indicated that the NADH dehydrogenase 4 and the ribosomal protein S12 genes could provide significant value as an early diagnostic marker for human cervical cancer and to define a molecular margin for progressive disease. Furthermore, during the postoperative follow-up of patients with localized cancer of the uterine cervix the measurement of NADH 4 or ribosomal protein S12 might lead to the early detection of recurrent disease when curative therapy is still an option.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Genes that are over-expressed in squamous cell carcinoma

| Differential display | Reverse Northern Blot | cDNA microarray | Best match in GenBank database (Accession Number) |
|---|---|---|---|
| G30CA | G30CA | G30CA | Human 16S ribosomal RNA (6137796) |
| G30CB | G30CB | | Human EST yu04f09* (H72762) |
| G30CC | G30CC | G30CC | Human ribosomal protein S12 (RPS12) mRNA (NM_001016) |
| G30CD | G30CD | G30CD | Human mRNA for collagenase (X05231) |
| G30CE | G30CE | G30CE | No match |
| G30CH | G30CH | G30CH | Human ZNF01 and HUMORFKGIB genes (AF205588) |
| G30CI | G30CI | G30CI | Human guanine nucleotide binding protein β5 (GNB5) (NM_006578) |
| G30CJ | | G30CJ | Human ribosomal protein L13a (RPL13A) mRNA (NM_012423) |
| G30CK | G30CK | | No match |
| G30CM | | | Human chromosome X clone RP1-298J18 (AL096764) |
| G31C1 | | G31C1 | Human STS WI-15569 (G21217) |
| G31C2 | | G31C2 | No match |
| G31C3 | | G31C3 | No match |
| G31C4A | | | Human GAP-associated tyrosine phosphoprotein p62 mRNA (NM_006559) |
| G31C4B | | G31C4B | Homo sapiens chromosome 1 clone RP4-758N20* (AL03705) |
| G31C4C | G31C4C | | No match |
| G31C5A | | | Human transmembrane protein BRI (BRI) mRNA (AF152462) |
| G31C5B | G31C5B | | No match |
| G31C5C | G31C5C | G31C5C | No match |
| G31C5D | G31C5D | | No match |
| G31C5E | G31C5E | G31C5E | Human capping protein muscle Z-line, α1 mRNA (NM_003832) |
| G31C5F | | | No match |
| G31C5G | G31C5G | G31C5G | No match |
| G31C5H | | G31C5H | Human gene for casein kinase II subunit β (X57152) |
| G31C6A | G31C6A | G31C6A | Human L-3-phosphoserine-phosphatase homo (CO9) Mrna (NM_003832) |
| G31C6B | G31C6B | | Human EST zh46b08.sl* (W93382) |
| G32C2A | G32C2A | | No match |
| G32C2B | G32C2B | G32C2B | Human general transcription factor IIB (GTF2B) mRNA (NM_001514) |
| G32C2C | G32C2C | G32C2C | Human clone 3A ETS-like protein mRNA* (U30172) |
| G32C3A | G32C3A | | Human cDNA FLJ10841 fis, clone NT2RP4001339 (AK001703) |
| G32C3B | G32C3B | | Human NADH dehydrogenase subunit 6 (6137796) |
| G32C3C | | G32C3C | No match |
| G32C4A | | G32C4A | Human mRNA for KIAA1311 protein (AB037732) |
| G32C4B | G32C4B | G32C4B | Human NADH dehydrogenase subunit 4 (6137796) |
| G32C4C | | | No match |
| G32C4D | G32C4D | G32C4D | No match |
| G32C4E | | | Human chromosome 17, clone HCIT48C15 (AC003104) |
| G32C5A | G32C5A | G32C5A | No match |
| G32C5B | | | Human S1H003 mRNA (AF077040) |
| G32C6 | G32C6 | G32C6 | Human ubiquitin specific protease 3 (USP3) mRNA (NM_006537) |
| G32C7 | G32C7 | G32C7 | Human procollagen-proline, 2-oxoglutarate 4-dioxygenase (proline 4-hydroxylase), α polypeptide 1 (P4HA1) mRNA (NM_000917) |

*The homologous sequence is in reverse orientation with respect to the cDNA fragment.

TABLE 2

Cloned cDNA fragments and their Reverse Northern Blot analysis

| Clone | Size of cDNA (bp) | Fold amplified in cancer tissue | cDNA fragment sequence | |
|---|---|---|---|---|
| G30CA | 204 | 2.08 | AAGCTTGGTGACAGCTGGTTGTCCAAGATAGAATCTTAGTTCAACTTTAAATTTGCCCACAGAACCCTCTAAATCCCCTTGTAAATTTAACTGTTAGTCCAAAGAGGAACAGCTCTTTGGACACTAGGAAAAAACCTTGTAGAGAGAGTAAAAAATTTAACACCCATAGTAGGCCTAAAAGCAGCCACCAAAAAAAAAAAGCTT | [SEQ ID NO:5] |
| G30CB | 207 | 2.64 | AAGCTTGGTGACATAGTATGGTAATAACAATCATCAAACATCTTTAGTTGACAAGAATTTGAAATGGGATAGTGGGGCCGGGCGCAGTGGCTCATGCTGTAATCCCAGCAATAAGTGAGGCCTAGATGAGCAAATCACTGGAGCCCAGAAGTTCGAGACCAGCCTGAGCAACATGACGAAACCCCGTCTCTACAAAAAAAAAAAGCTT | [SEQ ID NO:6] |
| G30CC | 204 | 1.94 | AAGCTTGGTGACAACAAGAAACTAGGAGAATGGGTAGGCCTTTGTAAAATTGACAGAGAGGGGAAACCCCGTAAAGTGGTTGGTTGCAGTTGTGTAGTAGTTAAGGACTATGGCAAGGAGTCTCAGGCCAAGGATGTCATTGAAGAGTATTTCAAATGCAAGAAATGAAGAAATAAATCTTTGGCTCACAAAAAAAAAAAGCTT | [SEQ ID NO:7] |
| G30CD | 207 | 3.00 | AAGCTTGGTGACAAACATATCCTTTCAAGACAGAAAGAGACAGGAGACATGAGTCTTTGCCGGAGAAAGCAGCTCAAGAACACATGTGCAGTCACTGGTGTCACCCTGGATAGGCAAGGGATAACTCTTCT | [SEQ ID NO:8] |

TABLE 2-continued

Cloned cDNA fragments and their Reverse Northern Blot analysis

| Clone | Size of cDNA (bp) | Fold amplified in cancer tissue | cDNA fragment sequence | |
|---|---|---|---|---|
| | | | AACACAAAATAAGTGTTTTATGTTTGGAATAAAGTCAACCTTGTTTCTACTGTTTTATACAAAAAA<br>AAAAAGCTT | |
| G30CE | 206 | 4.27 | AAGCTTGGTGACAGGAATAGAAAATGGTACAGCCACTGTGGGAAACAGTTTGGCAGTTCTTTAGAAA<br>GCTGAACATAGAATTACCATAGGATCTAGCAGTTCTTCTAGGTACATACCCCAAAGAATTGAAAGCA<br>AGGACTTGAACAGATATTTGTACACCCATGTTCATAGCAGCAGTTTTCACAACAGCCAAAAAAAAAA<br>AGCTT | [SEQ ID NO:9] |
| G30CH | 202 | 3.55 | AAGCTTGGTGACACTGAGCAAATAAATATGTTGAGAATGATGACAGCAAGATTTCTCCATTAGAGAA<br>GGTATTTATAAAAATAGGAATGAGGAGAGCTAGAAACCCTGGAGTGTGGCATTAGAATAGAACTCAT<br>ATCTTTTAAATATATAGGAACAAATAAATAAATTGTTGTGTGTGCACATATGCAAAAAAAAAAAGCT<br>T | [SEQ ID NO:10] |
| G30CI | 207 | 2.13 | AAGCTTGGTGACAAGAAAGCCATGGTGTGGGACATGCGCTCCGGCCAGTGCGTGCAGGCCTTTGAAA<br>CACATGAATCCGACATCAACAGTGTCCGGTACTACCCCAGTGGAGATGCCTTTGCTTCAGGGTCAGA<br>TGACGCTACGTGTCGCCTCTATGACCTGCGGGCAGATAGGGAGGTTGCCATCTATTCCAAAAAAAAA<br>AAGCTT | [SEQ ID NO:11] |
| G30CK | 206 | 1.68 | AAGCTTGGTGACATAGCAAGACTCTGTCTAAAAAAAAAAAAAAAAAACCTACTATAGGCCTGCAATA<br>GTGCCTCATGCCTGTAATCCCAGCACTATGGGAGGCCAAAGTGGGAGGATTGCTTGAGACTAGGAGT<br>TTGAGACCAGCCTGGGGAACATAACGTGACCCTGTTTCTACCAACACCCCCGCCCCAAAAAAAAAA<br>AGCTT | [SEQ ID NO:12] |
| G31C4B | 258 | 1.67 | AAGCTTAGTCAAGXGGAAGGAATTGATACAAAAXXXXGAGGGGCTAATTATAGAAXXCAAGTCCCTT<br>CGTAGGTGTGGGAGATAATCCAGTGCATAATTGGAGGAGTTAGTCTTTXAAAGTATATGACCATGGA<br>GTGGTTGGCTGTGTGTGGTGGAAGAAAAGATAATTAGAAATGCAGGCATTCAAAGAACTTAAAGGCC<br>ATATGTTAAGATATTTTAAGCCTTAAGACTGGATGxGTTACCAAAAAAAAAAAGCTT | [SEQ ID NO:13] |
| G31C4C | 254 | 1.65 | AAGCTTAGTCAAGTACATTAAATGGCATTCAAGTTGAAAAAGAAGTTAAACTATCTGTTTACAAATG<br>ACATGATCTTATCTATAGAAAATCACAAGGGAAATCACAAAAATCTGTTAAAACTAATGATCGAGTT<br>CAGCAAGTTGCAGAATACAAGTTCAATACACATAAATATATTTCTAGACAGTTGCAATGAACATACA<br>AAAATGAAATTACAAAAAACGGTTGTTACCAATAACTCAAAAAAAAAAAGCTT | [SEQ ID NO:14] |
| G31C5C | 183 | 1.65 | AAGCTTAGTCAAGAGGCATAAAGGTTTAGCAXGTTAAGGCAGAGATATAGATGXTTTTTAGAAAGGT<br>CTAAATCAATTCCTAGAAAXAAAAATATACTGAGATTATCAGATTATGCATTGCAGAAGGTTAGAT<br>TAGTGATCTTGAAGCATAATCATAGAATGTATCAAAAAAAAAAAGCTT | [SEQ ID NO:15] |
| G31C5D | 176 | 2.31 | AAGCTTAGTCAAGGCAAAATAACAAAAGGATTAAAAATAAAATAATGACCAGCAATATATCAGAAAA<br>CAAAACAGGGAAAGAAATCAGTTAGCTGACCTAGATCTCAGACAAAGTAGAAAATAAGACAAAACAC<br>TTTCTCCCCTCATCTCTGCTCACCCCCAAAAAAAAAAAGCTT | [SEQ ID NO:16] |
| G31C5E | 179 | 3.57 | AAGCTTAGTCAAGCAAGTTTGTTCCAGGTGACCCATTGAGCTGTGTATGCATTTTTGTTTATTTCA<br>ATAAAAATATATTTGTATTATTTGTCCTTCATACTATCCATCCATACCACACTATCTTCTGTATCAG<br>GTAGTCTAATAGAAATATACCTGTTTTGTTCCAAAAAAAAAAAGCTT | [SEQ ID NO:17] |
| G31C5G | 179 | 4.25 | AAGCTTAGTCAAGAGGAAGAGGTAATGCCTTTAAGTTAAAGGCCGGTCAAACACGATGACTCACAC<br>CTGTAATTCCACTATAAATAACTAAGGCAGGAGGATCACTTGAGCCTAGGAGTTTGAGACAGCCTA<br>AATAACACAGCAAGACGGTGTCTCCATATATCAAAAAAAAAAAGCTT | [SEQ ID NO:18] |
| G31C6A | 242 | 2.58 | AAGCTTAGTCAAGGATAACGCCTAAATGGTATATCACTGATTTTGTAGAGCTGCTGGGAGAACCGG<br>AAGAATAACATCCATTGTCATACAGCTCCAAACAACTTCAGATGAATTTTTACAAGTTACACAGAT<br>TGATACTGTTTGCTTACAATTGCCTATTACAACTTGCTATAGAAAGTTGGTACAGATGATCTGCAC<br>TGTCAAGTAAACTACAGTTAGGAATCCTCAAAAAAAAAAAGCTT | [SEQ ID NO:19] |
| C31C6B | 243 | 2.33 | AAGCTTAGTCAAGGTATCAAGATTTTCTTCATGCCATTACTACAGAAACAGGGTAGAATACTCATAG<br>TTCTTCGGCTCAAGAGCAGCAGAGAGTTTCTGACAAGTATTTTTGCATTTGGTAAAATGGTAGTCTA<br>AGTTGGAACTCAGTAAACATATTTTTGTTTTCAATGAGGGGAAGTGTAGAACTGTAGTACTCTCAAAT<br>TATTTTTTCTCAAATTGGCCTTTGTGCAAAAAAAAAAAGCTT | [SEQ ID NO:20] |
| G32C2A | 312 | 1.78 | AAGCTTCCACAGCCACCTGTGTATACTTCCATTATGGCATGTAACATGCTGGCAAGAAATTGATTCAT<br>TGGGTTGTGTCTTCTCAGCTGCCTGAAGAATGAAATCATATACTCTAGTTTCATATGCCCAGCATTG<br>TACACAACTTGACACATCACAGCAGCTCTAGGAAAGCACATAGGCTGACAACTGAGTGAACAACCCA<br>CTGACTGTGTGTCGTCAGGGTTGGGAAAGCAAGGGCAGGTCTCTGTGCCCCATCTCTAGCTTTTCC<br>TCAACTTAGGCTTTATAAACCCTTGCATCAAAAAAAAAAAGCTT | [SEQ ID NO:21] |
| G32C2B | 311 | 2.44 | AAGCTTCCACAGCTATAAATTGAGGCAGCTAACGTCAAATTCTTGAATACAAAACTTTGCCTGTTGT<br>ACATAGCCTATACAAAATGCTGGGTTGAGCCTTTCATGAGGAAAAACAAAAGACATGGTACGCATTC<br>CAGGGCTGAATACTATTGCTTGGCATTCTGTATGTATACTATGTGAAACATATTTAATGATTTAA<br>ATTTCTTATCAAATTTCTTTTGTAGCAATCTAGGAAACCTGGTATTTTGGAAGATATTTGAAATTATG<br>TAATTCTTGAATAAACATTTTCGAACTCAAAAAAAAAAAGCTT | [SEQ ID NO:22] |
| G32C2C | 284 | 1.56 | AGGCAGCCGGACTCCCTGTCTCACCTACATTAACCCATGCATACTGTATGCCAATAAACTCACTTTG<br>GTATATCCGGCGTCACATGCAGAGAGGAACTCTGCGNGNCAAAGTGTTGCTTCTTAAAGTTTCATTA<br>TTGGCAACTAGAGGGTTGTTTTAATGCATGGAAACTAAACAGATTCCTCGGGGAGTTCCTGAAGGA<br>ACCAGGTGGGCAAACCTTTGCTTATATACATGCGGCCTCACCTGGAAGAGAAATAAACCACTTGTAC<br>CAAAAAAAAAAGCTT | [SEQ ID NO:23] |
| G32C3A | 307 | 2.00 | AAGCTTCCACAGCATCCATTGTTGAAATAACCATTTTCAGTTGTGATGCCTTAACTAAGAAGCCAAT<br>TGTTAGCCTGAAATGCAATCTTGGTAGCCAGTTTCAATGAAGCTAGAGATTAGTCAGAAAAGTTAG<br>CTGTTGGGCTTTAGAAAGGNNTTTTGAGTCCTGTCATTTCTACTTGGGAGCATTTTGGAGCAGATTA<br>GTCTTTCAGTATAAAAACAAGTGGCTACCTGATGGAAACTTTTCCTACCCTTATAGGAAACTGAGCA<br>CAAGCTGAATGATATTGCTGCTGCAAAAAAAAAAAGCTT | [SEQ ID NO:24] |
| G32C3B | 310 | 1.74 | AAGCTTCCACAGCACCATCCTACCTCCATGCTAACCCCACTAAAACACTCACCAGACCTCAACCCCT<br>GACCCCCATGCCTCAGGATACTCCTCAATAGCCATCGCTGTAGTATACCCAAAGACAACCATCATTC<br>CCCTAAATAAATTAAAAAAACTATTAAACCCATATAACCTCCCCAAAATTCAGAATAATAACACA<br>CCCGACCACACCGCTAACAACCAATACTAAACCCCCATAAATAGGAGAAGGCTTAGAAGAAACCCC<br>ACAAACCCCATTACTAAACCCACACTCAAAAAAAAAAAGCTT | [SEQ ID NO:25] |

TABLE 2-continued

Cloned cDNA fragments and their Reverse Northern Blot analysis

| Clone | Size of cDNA (bp) | Fold amplified in cancer tissue | cDNA fragment sequence | |
|---|---|---|---|---|
| G32C3C | 303 | 2.97 | AAGCTTCCACAGCCCACTGACTCAAATGGTAATCTCTTTTGGCAACACCCACACAGACACACCCAGG ATTAATACTTTGTATCCCTCATTCCAATTAAGTTGACACTCAGTATTAACCATCATATATGGCAACA TATCTTTCTGGATAGGACCTAGAGAAACTTTCAAATAATGACTTGTAACTTCTCTACACTGAAGGAA TATATACACAATTTGTAATTTAATTTTGAGTGTATATTGACAAACTACATGTATCTACAAATTACCT TTAATTCAATTGCAACCCTCAAAAAAAAAAAGCTT | [SEQ ID NO:26] |
| G32C4B | 260 | 3.94 | AAGCTTCCACAGCCACAGAACTAATCATATTTTATATCTTCTTCGAAACCACACTTATCCCCACCTT GGCTATCATCACCCGATGAGGCAACCAGCCAGAACGCCTGAACGCAGGCACATACTTCCTATTCTAC ACCCTAGTAGGCTCCCTTCCCCTACTCATCGCACTAATTTACACTCACAACACCCTAGGCTCACTAA ACATTCTACTACTCACTCTCACTGCCCAAGAACTATCAAACTCCAAAAAAAAAAAAGCTT | [SEQ ID NO:27] |
| G32C4D | 264 | 1.58 | AAGCTTCCACAGCACCAACAAAAGTTAACGTTGCATGTTTCACTATTTGGTTTTTAACCTACATTC CAAATGGCTTTTACAACAGTTATAATAAAATGATAACTGCAAAGGCATTGTGTAGCTAAATGAAAA TGTTGTAAATGTGATAATGAAACACGGCCAAAGTTTTGACAATTAGGCAATAGATGGAGATAAAAA TTTTAGACTAAAGTGTACAATAAAATACACACACAGCCAAACTCACTCCAAAAAAAAAAAGCTT | [SEQ ID NO:28] |
| G32C5A | 257 | 1.62 | AAGCTTCCACAGCAACAACCAACATAGCTAATACAGAAAGCAGTCAGCAGACTCTACAGAATTCCC AGTTTCTTTTAACAAGGTAGCTCATTTGTTAATAGAATTTTGTTTGGGAAGTAATATTTTATTGCC ACTACAGTCTGGAATTATCTTTTCTCTTTTGTGCATTATATTTCTTAAAATTTTGTGTTTGATTAA AACTCACAGATCTCTGATTAAAACGCATATTCAGTACTTTCCCCAAAAAAAAAAAGCTT | [SEQ ID NO:29] |
| G32C6 | 250 | 1.93 | AAGCTTCCACAGCTATAATGGACATCAGGTTGACTCTAAATCAAGGATCATGTGTGCACAATACTTG TGGCCCACAAAATTTCACAATGACTGCTGAGGAATCATTCTTTTTGCCTGTAAAATATAACAAAGGG CATCATTAAGTAGACCAGGTAATTACTGCTTGTCTCTCAAGGCTGCTGTCTTTATCAGCACTAACTA AATAAATTTGTTGGTTCAGTTGTACTTGTCCTGCAAAAAAAAAAAGCTT | [SEQ ID NO:30] |
| G32C7 | 224 | 2.23 | AAGCTTCCACAGCAGAGGAATTACAGGTAGCAAATTATGGAGTTGGAGGACAGTATGAACCCCATTT TGACTTTGCACGGAAAGATGAGCCAGATGCTTTCAAAGAGCTGGGGACAGGAAATAGAATTGCTACA TGGCTGTTTTATATGAGTGATGTGTCTGCAGGAGGAGCCACTGTTTTTCCTGAAGTTGGAGCTAGTG TTTGGCCCAAAAAAAAAAAGCTT | [SEQ ID NO:31] |

BIBLIOGRAPHY

Anton-Culver et al., 1992, *Am. J. Obstet. Gynecol.* 166: 1507-1514.
Boring et al., 1994, *CA Cancer J. Clin.* 44: 7-26.
Berek et al., 1981, *Cancer* 48: 2734-2741.
Bethwaite et al., 1992, *Br. J. Obstet. Gynaecol.* 99: 745-750.
Brisson et al., 1994, *Am. J. Epidemiol.* 140: 700-710.
Burke et al., 1987, *Obstet. Gynecol.* 69: 382-385.
Canavan and Doshi, 2000, *Am Fam Physician* 61: 1369-1376.
Douillard and Hoffman, 1981, Basic Facts about Hybridomas, in Compendium of Immunology Vol. II, ed. by Schwartz.
Duggan, 1998, *Eur J Gynaecol Oncol.* 19: 338-344.
FIGO News, 1987, In *J. Gynaecol Obstet* 25: 87.
Gallup et al., 1985, *Obstetrics and Gynecology* 65: 416-422.
Goodman et al., 1989, *Gynecol. Oncol.* 33: 241-247.
Gustafsson et al., 1989, *Br. J. Cancer* 60: 132-141.
Herrington et al., 1995, *Cytopathlology* 6: 176-189.
Ho et al., 1998, *N. Engl. J. Med.* 338: 423-428.
Kohler and Milstein, 1975, *Nature* 256: 495-499.
Kohler and Milstein, 1976, *European Journal of Immunology* 6: 511-519.
Kjaer et al., 1997, *Cancer Epidemiol. Biomark. Prev.* 6: 799-805.
Krivak et al., 2000, *Gynecol. Oncol.* 77: 334-335.
Lazo, 1999, *Br. J. Cancer* 80: 2008-2018.
Lanciano, 1996, *J. Natl. Cancer Inst. Monogr.* 21: 113-115.
Liang et al., 1994, *Nucl. Acids. Res.* 22: 5763-5764.
Ostor, 1993, *Int. J. Gynecol Pathol.* 12: 186-192.
Piamsomboon et al., 1996, *Anticancer Drugs.* 7: 800-804.
Pisani et al., 1993, *Int. J. Cancer* 55: 891-903.
Pisani et al., 1997, *Cancer Epidemiol Biomarkers Prev.* 6: 387-400.
Poynor et al., 1995, *Gynecol Oncol.* 57: 158-164.
Rosl et al., 1989, *Mol. Carcinog.* 2: 72-80.
Scheffner et al., 1991, *Proc. Natl. Acad. Sci.* 88: 5523-5527.
Schiffman et al., 1993, *J. Natl. Cancer Inst.* 85: 958-964.
Siadat-Pajouh et al., 1994, *J. Histochem Cytochem.* 42: 1503-1512.
Soong et al., 1992, The *J. of Immunology* 149: 2008-2020.
Steren et al., 1993, *Gynecol Oncol.* 48: 355-359.
Strang et al., 1987, *Anticancer Research* 7(4B): 807-810.
Tay et al., 1997, *Singapore Med. J.* 38: 520-524.
Van Oortmarssen et al., 1991, *Br. J. Cancer* 64: 559-565.
Vizaino et al., 1998, In. *J. Cancer* 75: 536-545.
Werner-Wasik et al., 1995, *Int. J. Radiat. Oncol. Biol. Phys.* 32: 1309-1317.
Wingo et al., 1995, *CA Cancer J. Clin.* 45: 8-30.
Yazigi et al., 1990, *Obstet. Gynecol.* 75: 1012-1015.
Zaitoun et al., 2000, *J. Clin. Pathol.* 53: 191-196.

The invention claimed is:

1. A method for distinguishing between normal cervical tissue and cervical cancer tissue in a patient with stage 1B or 2A cervical cancer, the method comprising detecting differential expression of polynucleotides comprising SEQ ID NO:7 in cervical cancer cells relative to levels of polynucleotides comprising SEQ ID NO:7 in normal cervical epithelial cells, wherein cervical cancer cells demonstrate a net fold increase of at least 2 in levels of polynucleotides comprising SEQ ID NO:7 compared to matched normal cervical epithelial cells, thereby indicating the presence of stage 1B or 2A cervical cancer tissue.

2. A method of diagnosing a patient with stage 1B or 2A cervical cancer, comprising detecting differential expression of polynucleotides comprising SEQ ID NO:7 in cervical cancer cells relative to expression of polynucleotides comprising SEQ ID NO:7 in matched normal cervical epithelial cells, wherein when cervical cells demonstrate a net fold increase of at least 2 in levels of polynucleotides comprising SEQ ID NO:7 compared to matches normal cervical epithelial cells, said patient is diagnosed with stage 1B or 2A cervical cancer.

3. The method of claim 1 or claim 2, wherein the detection comprises RNA-RNA in situ hybridization.

4. The method according to claim 1 or claim 2 wherein the detection comprises cDNA microarray analysis.

5. The method according to claim 1 or claim 2 wherein the detection comprises Northern blot analysis.

6. The method according to claim 1 or claim 2 wherein the detection comprises reverse Northern blot analysis.

7. The method of claim 1 or claim 2, wherein the detection of polynucleotides comprises: isolating total RNA from cervical cancer tissue and cervical tissue from a normal individual; generating complementary DNA molecules using reverse transcriptase-polymerase chain reaction (RT-PCR), wherein said complementary DNA molecules comprise SEQ ID NO:7; subjecting said complementary DNA molecules to separation means such that the relative presence or absence of complementary DNA molecules can be detected from cervical cancer tissue relative to normal tissue; and detecting differential expression of SEQ ID NO:7.

8. A method according to claim 7, wherein a primer used in said RT-PCR is as set forth in SEQ ID NO: 1.

9. A method according to claim 7, wherein a primer used in said RT-PCR is as set forth in SEQ ID NO: 2.

* * * * *